(12) United States Patent
Nobbe

(10) Patent No.: US 12,083,031 B1
(45) Date of Patent: Sep. 10, 2024

(54) STABILIZING KNEE ANKLE TIBIAL EXOSKELETON

(71) Applicant: Ralph Nobbe LLC, Carpinteria, CA (US)

(72) Inventor: Ralph W. Nobbe, Carpinteria, CA (US)

(73) Assignee: Ralph Nobbe LLC, Carpinteria, CA (US)

( * ) Notice: Subject to any disclaimer, the term of this patent is extended or adjusted under 35 U.S.C. 154(b) by 0 days.

(21) Appl. No.: 18/121,400

(22) Filed: Mar. 14, 2023

Related U.S. Application Data

(60) Provisional application No. 63/445,802, filed on Feb. 15, 2023.

(51) Int. Cl.
    *A61F 5/00*     (2006.01)
    *A61F 5/01*     (2006.01)

(52) U.S. Cl.
    CPC .................................. *A61F 5/0127* (2013.01)

(58) Field of Classification Search
    CPC .... A61F 5/0127; A61F 5/0195; A61F 5/0585; A61F 5/0111; A61F 5/0113; A63C 10/04; A63C 10/06; A43B 3/16; A43B 3/18
    USPC .................................................. 602/27; 36/15
    See application file for complete search history.

(56) References Cited

U.S. PATENT DOCUMENTS

| | | | | |
|---|---|---|---|---|
| 6,214 A | * | 3/1849 | Yerger | A61F 5/0111 36/89 |
| 1,792,155 A | * | 2/1931 | Fisher | A61F 5/0111 602/28 |
| 4,320,748 A | * | 3/1982 | Racette | A61F 5/0585 602/23 |
| 4,505,057 A | | 3/1985 | Kiester | |
| 4,693,239 A | * | 9/1987 | Clover, Jr. | A61F 5/0127 602/27 |
| 4,771,768 A | * | 9/1988 | Crispin | A61F 5/0127 D24/190 |
| 5,056,509 A | * | 10/1991 | Swearington | A61F 5/0127 602/29 |
| 5,183,036 A | * | 2/1993 | Spademan | A43B 7/20 602/10 |
| 5,250,021 A | * | 10/1993 | Chang | A61F 5/0111 602/23 |
| 5,370,133 A | * | 12/1994 | Darby | A61F 5/0111 128/882 |
| 5,429,588 A | * | 7/1995 | Young | A61F 5/0127 602/10 |

(Continued)

FOREIGN PATENT DOCUMENTS

| | | |
|---|---|---|
| EP | 1993492 B1 | 10/2017 |
| ES | 2712738 T3 | 5/2019 |
| WO | WO2010/027407 A1 | 3/2010 |

*Primary Examiner* — Adam Baker
(74) *Attorney, Agent, or Firm* — Steinfl + Bruno, LLP

(57) ABSTRACT

Disclosed is an ankle foot orthoses (AFO) that can be configured for either posterior or anterior entry of a user's injured or malfunctioning leg and foot without removing shoe gear on that foot. The AFO comprises a shoe-receiving foot shell, a pair of vertical struts connected to the foot shell and multiple shoe and leg retaining straps or binders. The several straps or binders, which include adjustable closures, are attached to the foot shell and/or the vertical struts to provide the user with the ability to align, properly position, and support the leg and foot for preferred orientation of the injured or malfunctioning leg and foot during the healing process of the thereof.

28 Claims, 16 Drawing Sheets

(56) References Cited

U.S. PATENT DOCUMENTS

| | | | |
|---|---|---|---|
| 5,593,383 A * | 1/1997 | DeToro | A61F 5/0111 602/66 |
| 6,749,578 B2 * | 6/2004 | Peters | A61F 5/0127 602/5 |
| 7,125,392 B2 | 10/2006 | Scott | |
| 7,270,644 B2 | 9/2007 | Ingimundarson | |
| 7,458,950 B1 | 12/2008 | Ivany | |
| 7,744,513 B2 * | 6/2010 | Castellano | A61F 5/0195 482/79 |
| 7,753,864 B2 | 7/2010 | Beckwith et al. | |
| 8,021,317 B2 * | 9/2011 | Arnold | A43B 7/00 128/882 |
| 8,313,451 B2 | 11/2012 | Cox | |
| 8,465,445 B2 * | 6/2013 | George | A61F 5/0111 602/26 |
| 8,808,214 B2 | 8/2014 | Herr et al. | |
| 8,900,171 B2 | 12/2014 | Darby, II et al. | |
| 9,192,502 B2 | 11/2015 | Drillio | |
| 9,345,608 B2 | 5/2016 | Phillips | |
| 9,398,970 B1 | 7/2016 | Meyer | |
| 9,872,790 B2 | 1/2018 | Capra et al. | |
| 9,993,361 B2 | 6/2018 | Giontella | |
| 10,123,897 B2 | 11/2018 | Sutti et al. | |
| 10,433,999 B2 | 10/2019 | Hammerslag et al. | |
| 10,485,688 B2 | 11/2019 | Hassel et al. | |
| 10,632,006 B2 | 4/2020 | Elbaz et al. | |
| 10,743,621 B2 | 8/2020 | Wyatt et al. | |
| 10,874,539 B2 * | 12/2020 | LeCursi | B33Y 80/00 |
| 10,945,871 B2 | 3/2021 | Patterson et al. | |
| 11,178,935 B2 | 11/2021 | Iglesias et al. | |
| 2004/0145128 A1 * | 7/2004 | Couderc | A63C 10/24 280/809 |
| 2004/0232658 A1 * | 11/2004 | Poscich | A63C 10/285 280/618 |
| 2005/0131324 A1 * | 6/2005 | Bledsoe | A61F 5/0111 602/23 |
| 2005/0172517 A1 | 8/2005 | Bledsoe et al. | |
| 2006/0084899 A1 * | 4/2006 | Verkade | A61F 5/0111 602/5 |
| 2009/0069732 A1 * | 3/2009 | Jackovitch | A61F 5/0127 602/23 |
| 2010/0106065 A1 | 4/2010 | Ward | |
| 2011/0105969 A1 | 5/2011 | Nace | |
| 2011/0196277 A1 | 8/2011 | Savard et al. | |
| 2012/0116275 A1 * | 5/2012 | Pochatko | A61F 5/0111 602/27 |
| 2012/0253253 A1 | 10/2012 | DeHeer et al. | |
| 2014/0109443 A1 | 4/2014 | Fanchiang et al. | |
| 2015/0065934 A1 | 3/2015 | Bader | |
| 2016/0151176 A1 | 6/2016 | Unluhisarcikli et al. | |
| 2016/0175689 A1 * | 6/2016 | Chen | A63C 10/24 280/14.21 |
| 2016/0213506 A1 * | 7/2016 | Chen | A61F 5/30 |
| 2017/0216071 A1 | 8/2017 | Bader | |
| 2017/0296372 A1 | 10/2017 | Fay | |
| 2018/0318164 A1 | 11/2018 | Wu et al. | |
| 2018/0325212 A1 | 11/2018 | Walborn et al. | |
| 2019/0224032 A1 * | 7/2019 | Ferlic | A61F 5/0127 |
| 2019/0298564 A1 | 10/2019 | Van Der Wilk et al. | |
| 2019/0374365 A1 | 12/2019 | Wu et al. | |
| 2020/0323675 A1 | 10/2020 | Drewitz | |

* cited by examiner

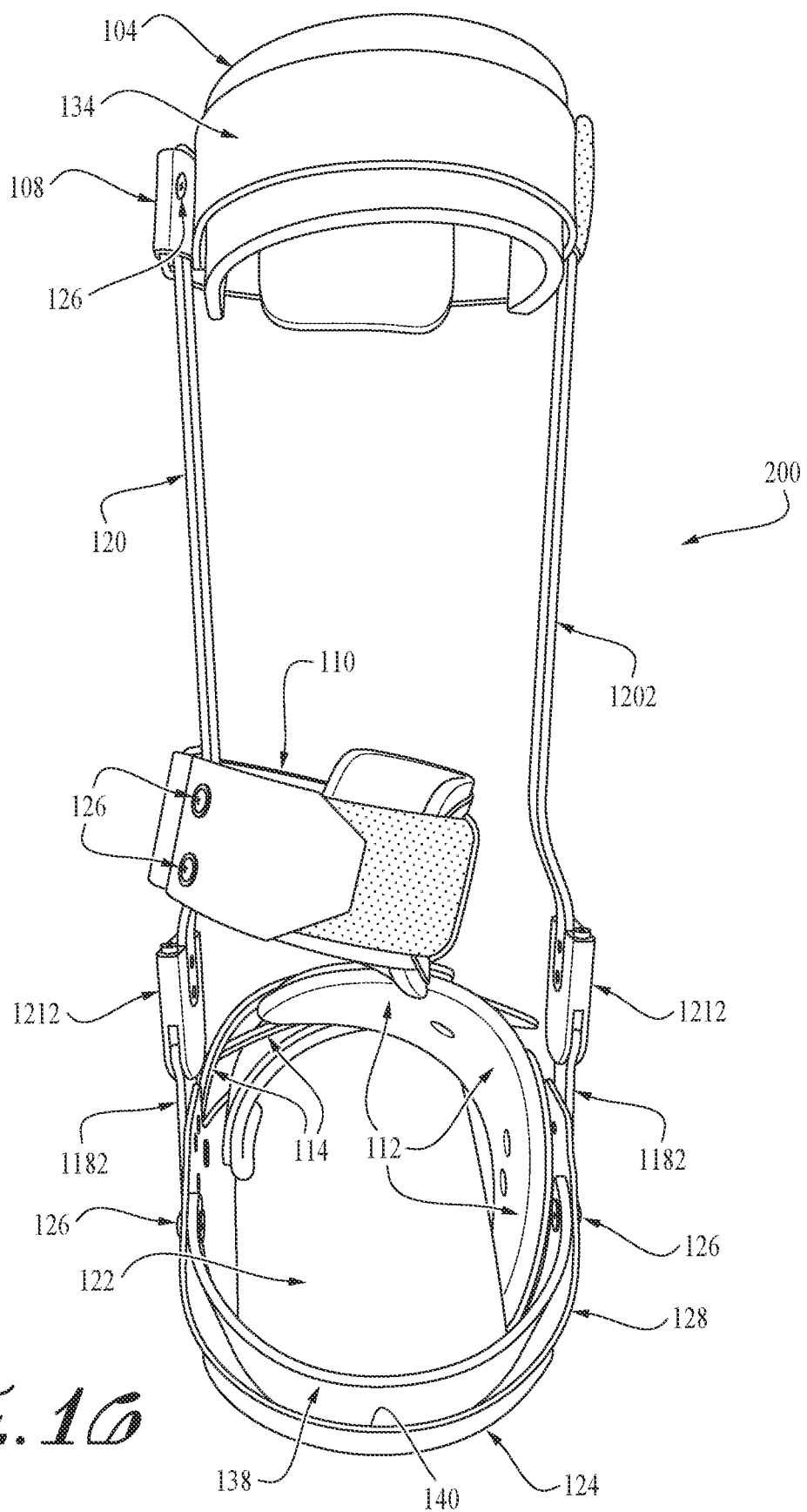

STABILIZING KNEE ANKLE TIBIAL EXOSKELETON

This application claims priority to U.S. Provisional Application 63/445,802 filed Feb. 15, 2023.

BACKGROUND

The SKATE™ Support System described herein was developed in response to observing challenges of individuals and their caregivers struggling with various custom, prefabricated and off the shelf ankle foot orthoses (AFO) designs. These challenges arise due to both specific footwear requirements and difficulty in donning the orthotic devices.

SUMMARY

The SKATE™ Support System was specifically designed to be worn over existing patient shoe gear but can also accommodate custom shoes. Major advantages are that it eliminates the need for a permanent shoe attachment with specialized shoe gear and can also eliminate the use of much larger, over-sized shoes which may be sized to accommodate various unilateral, internal AFOs and/or the use of different sized, also known as "split-sized", right and left shoes. However, it can require a compensatory sound side elevation (approximately 1 cm inside the shoe on the uninjured foot/leg); this has not been a problem for any patients, or clinicians to date, in experimental use. Prior art orthotic designs may also require use of a compensatory elevation in the sound side shoe. The SKATE™ Support System allows rapid semi-custom fabrication for acute needs and requires minimal clinician time for measurement, fit, or follow-up.

The SKATE™ Support System in the described embodiments includes a prefabricated metal skate platform of various sizes designed to fit the right or left foot and to receive the user's shoe. Double action ankle joints with stirrups fabricated from various assorted materials, such as Becker® double action ankle joints with stirrups, or similar devices, are attached to the foot shell of the SKATE™ Support System. Use of various materials for the foot shell, such as stainless steel, carbon composites, aluminum, titanium, and various plastic materials can accommodate patient specific strength, weight, biomechanical, and activity level requirements. Different closure systems, for example Velcro® fasteners, Click Medical Boa® dials, reel type closures, or adjustable ratchet binders for snowboard bindings are used, making available a custom double upright AFO with either clinician selected, varus or valgus control, and posterior or anterior entry. The various SKATE™ Support System AFO styles thus provide for heel first anterior entry or toe first posterior entry to address specific biomechanical patient requirements. The SKATE™ Support System is intended as a semi-custom, permanent orthosis to serve as an alternative to custom metal or plastic ankle foot orthoses as presently dispensed.

The several integral boot/sole designs shown and described herein include various rockers, wedges, and sole offsets, according to clinician request and designed to meet individual patient bio-mechanical gait requirements. The SKATE™ Support System can also incorporate custom molded patella tendon bearing brims (PTB) or custom calf lacer designs to axially offload foot/ankle pressure and distribute pressures onto the extremity. It may use various materials such as thermoplastic or composites structures with or without soft interfaces and It may incorporate an anterior swing band or hinged shell for donning or biomechanical purposes. Custom upper AFO designs of the SKATE™ Support System are fabricated to accommodate all sizes and alignment requirements.

BRIEF DESCRIPTION OF DRAWINGS

FIGS. 10-16 are images of an embodiment of the SKATE™ Support System configured for anterior entry for application to the left or right leg. These images also depict devices configured with varus control to provide medially directed support against varus instability for the right leg. The SKATE™ Support System can also be altered to provide laterally directed support for valgus control by altering the closure placement and direction of pull according to clinician request, preference, and biomechanical need.

FIG. 1 is a top view of a posterior entry embodiment for application of the SKATE™ Support System.

FIG. 2 is a right medial side rear perspective view of the posterior entry SKATE™ Support System of FIG. 1.

FIG. 3 is a right lateral side rear perspective view of the posterior entry SKATE™ Support System of FIG. 1.

FIG. 4 is a rear view of the posterior entry SKATE™ Support System of FIG. 1.

FIG. 5 is a right medial side view of the posterior entry SKATE™ Support System of FIG. 1.

FIG. 6 is a right lateral side view of the posterior entry SKATE™ Support System of FIG. 1.

FIG. 7 is a front perspective view of the-right medial side of the posterior entry SKATE™ Support System of FIG. 1.

FIG. 8 is a front perspective view of the right lateral side of the posterior entry SKATE™ Support System of FIG. 1.

FIG. 9 is a front view of the posterior entry SKATE™ Support System of FIG. 1.

FIG. 10 is a top view of an anterior entry SKATE™ Support System.

FIG. 11 is a right-side lateral rear perspective view of an anterior entry SKATE™ Support System of FIG. 10.

FIG. 12 is a right side medial rear perspective view an anterior entry SKATE™ Support System of FIG. 10.

FIG. 13 is a right side front lateral perspective view of an anterior entry SKATE™ Support System of FIG. 10.

FIG. 14 is a right side front medial perspective view of an anterior entry SKATE™ Support System of FIG. 10.

FIG. 15 is a right-side medial view of an anterior entry SKATE™ Support System of FIG. 10.

FIG. 16 is a rear view of an anterior entry SKATE™ Support System of FIG. 10.

DETAILED DISCUSSION

Figure 1:
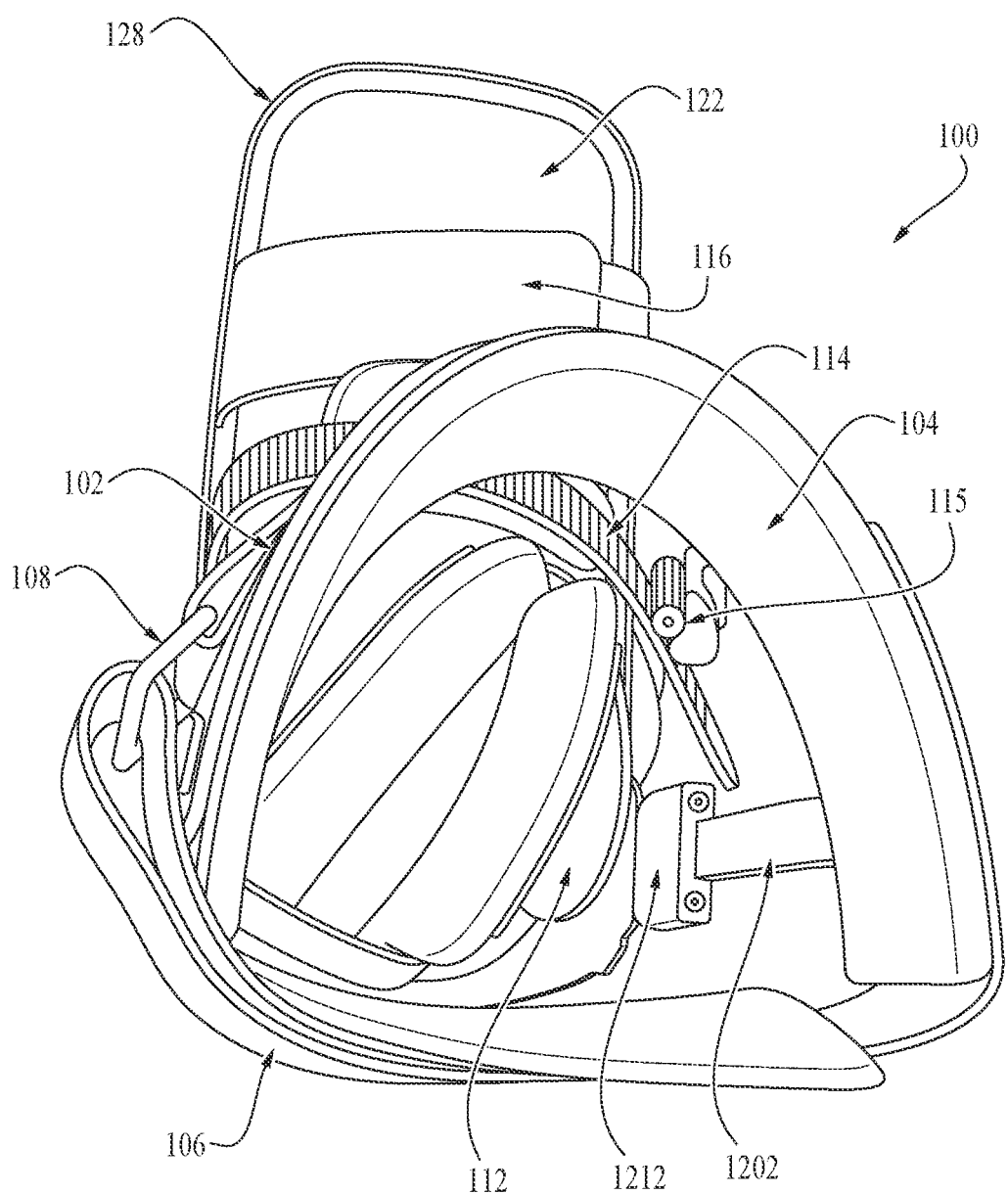
FIGS. 1-9 are images of an embodiment of the SKATE™ Support System configured for posterior entry for application to the left or right leg.

The orthotic devices described herein are intended to address the significant problems experienced by disabled or impaired patients, and of their caregivers in regard to their ability to apply an exterior, temporary, or permanent, support to an injured lower leg following repair of an injury and during the subsequent healing and rehabilitation process of neuromuscular and/or orthopedic impairments. A current device, referred to as a boot walker, intended for shorter term immobilization, can be difficult to properly apply and frequently requires the assistance of a second individual to assure proper installation so as to provide suitable structural support without causing pain or additional injury to the limb from improper application. These boot walkers are commercially available and are intended to be interim in use.

For example, following an ankle fracture a boot walker may be typically applied to the injured ankle, followed by a custom Arizona® ankle foot orthosis (AFO), a custom plastic or a metal AFO. Alternatively, following a cerebral vascular accident (CVA) or traumatic brain injury, multiple sclerosis, spinal injury, or similar neurological injury a custom Arizona® ankle foot orthosis (AFO) a custom or prefabricated plastic or composite internal fit AFO or a metal AFO may be prescribed. Each may have specific biomechanical designs which can also be incorporated into the SKATE™ Support System to meet clinician specified requirements. Conversations with patients struggling to apply various AFO's prescribed at different times during progression of their rehabilitation, and the ongoing complaints of patients/families and caregivers, clearly evidenced the need for suitable, adjustable support devices such as described and shown herein which provide to a user a greater self application ability as well independent doffing ability. Despite realized benefits, the donning and doffing difficulties, the shoe gear challenges herein described, have often led to rejection of AFO's described in prior art and used historically.

The devices described herein, while focused upon the needs of neurologically impaired individuals such as those suffering from a stroke, spinal cord injury, or traumatic brain injury (TBI) are not limited to such use and are applicable to injuries to the lower extremities including, but not limited to, bone fracture, mal- or non-union, post-operative care, wound care, failed surgeries or complications of surgeries, or tissue or muscle injury to the foot or lower leg. Traditionally, AFO's are designed either to wear inside shoe-gear or are attached permanently onto shoes. In such designs, this creates several known limitations.

Depending upon the internal AFO biomechanical design requirements, shoes may need to be up to two or more sizes larger and have a removable innersole to accommodate the additional bulk of the device. This creates a further obstacle in either purchasing mis-matched, split sized shoes or the use of over-sized shoes, particularly on the uninvolved foot which further adversely impacts gait. Placing an AFO within shoe-gear also makes donning of the shoe/AFO assembly more difficult for most individuals and their caregivers. Further, these internal AFO's are optimized around the specific heel height and innersole contours of the patient specific shoe-gear making replacement difficult as manufacturers often change or discontinue styles. Internal AFO's may also have a thick plantar surface which may require a compensatory elevation on the sound side.

Attaching the AFO externally and permanently to the shoe limits the AFO user to just that one pair of shoes and requires more substantial and costly shoe-gear to allow permanent attachment. Further when the shoe(s) become worn, costly and inconvenient replacement of permanently attached shoe gear is required. This often leaves the individual without use of their orthotic device pending shoe replacement. These specialized replacement shoes, suitable for orthotic attachment are costly, are becoming increasingly difficult to purchase and most often are not available under private or government, health insurance policies.

Many of the components described herein that are used to assemble and attach the various embodiments of the SKATE™ Support System 100, 200 to an individual's extremities are commercially available as they are used in similar but different applications in the construction and assembly of orthotic devices and sports equipment (i.e., ski-boots, snow board bindings and boots, biking equipment, boots, climbing equipment, etc.). However, those components have particular designs, shapes and structural requirements for each of the other intended purposes and must be modified, customized and/or structurally reconfigured for the AFO assemblies and purposes set forth herein. The modifications applied thereto would not necessarily be obvious to one skilled in the art and the final configuration of the components are driven by the special needs of the intended SKATE™ Support System 100, 200 device embodiments and require hindsight of the inventor/fabricator to adapt, bend, modify and customize a prior component to its new intended purposes in constructing the various embodiments of the SKATE™ Support System 100, 200.

An AFO for posterior entry (an injured leg is placed therein toes-first through the rear of the structure), referred to as a SKATE™ Support System 100, is shown in several different views in FIG. 1-9. An AFO for anterior entry, (an injured leg is placed therein heel first through the front of the structure), referred to as a SKATE™ Support System 200, is shown in several different views in FIGS. 10-16. While the Figures show the SKATE™ Support System 100, 200 configured for a particular leg, it can be assembled for placement on either a right leg or a left leg, the assembly for the opposite leg being a mirror image of the other leg with the primary difference being the location or orientation of buckles 108 on the calf strap 104 and the varus/valgus control panel/strap 112 (best shown in FIGS. 4 and 5) in an exterior location (i.e., not between the legs). This provides to the user easier access by the hands/arms on the same side as the injured foot/leg.

Figure 10:
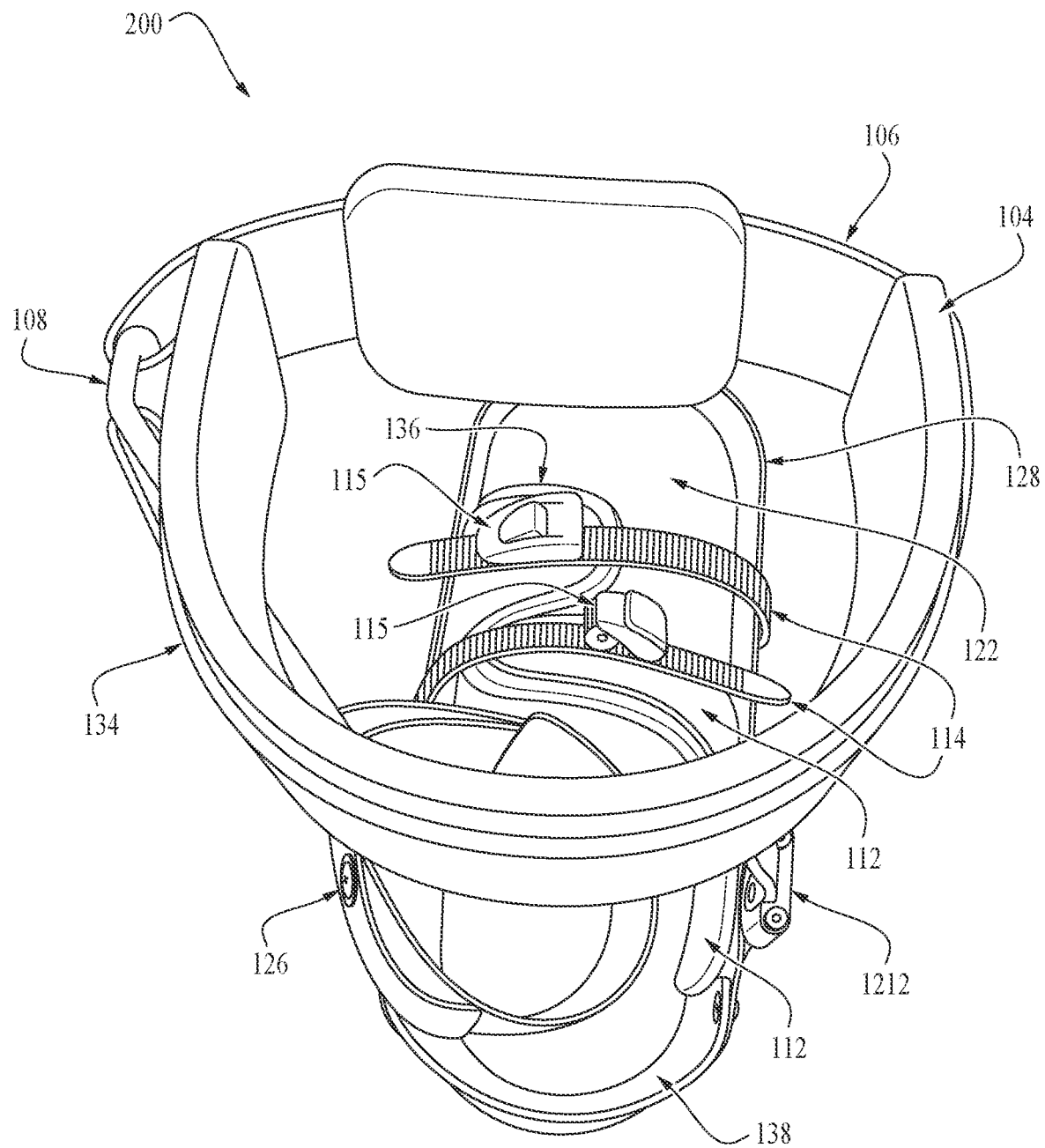

The varus/valgus control panel 112, which is a strap attached to a left or right (medial or lateral) skate shell 128 and the ankle strap 114 is provided to exert a directional force to the extremity. When the distal part of a limb is more lateral, it is referred to as valgum; when it is more medial, it is referred to as varum. When looking at lower extremity joints of the body, knee varum or valgum alignment is determined by looking at knee alignment. In a varum knee position the foot in relation to the knee is angled inward for a bowlegged presentation. A varum orientation shifts the weight line medially which can cause more force and weight bearing on the medial part of the knee and specifically, the medial meniscus and stresses the lateral collateral ligament. A valgum knee is where the foot in relation to the knee is angled outward for a knock-kneed appearance. The valgum alignment shifts the weight line laterally which can cause more force and weight bearing on the lateral part of the knee and specifically, the lateral meniscus. In the ankle, abnormal medial and lateral displacements are referred to as varus and valgus. As best shown in FIG. 10 toe panel 136 encompasses either the great toe or passes over the little toe, dependent upon whether intended for varus or valgus configuration. The panel 112, in a preferred embodiment, is comprised of a flexible polyethylene material with a pad liner similar to the ankle control strap 110. The varus/valgus control panel 112 creates a third point of pressure. For, example a Varus control pressure system would encompass the great toe, lateral ankle and inner calf creating three point pressure system.

The ankle strap 110 when used with the varus/valgus control panel 112 can be placed such that it is installed laterally to apply a medially directed force to stabilize against ankle varus instability. Conversely attaching ankle strap 110 and varus/valgus control panel 112 medially can exert a laterally directed force against ankle valgus. A varus ankle may be described as a "high arch foot" with a lateral instability, while a valgus ankle typically may be described as a "flat foot" with a medial instability.

The SKATE™ Support System 100, 200 is primarily intended to be worn over a patient's existing shoe-gear. The SKATE™ Support System 100, 200 can accommodate most functional shoe-gear except for; high heels, sandals, slippers, and other shoe-gear not generally considered appropriate or safe for medical use by injured individuals. In preferred embodiments the SKATE™ Support Systems 100, 200 incorporates a posterior or anterior entry foot shell 128 composed of a thin, light weight metal, composite, or plastic material. A low friction shoe interface 122 is attached to an upper surface of the foot shell 128; applied to the bottom surface of the foot shell 128 is coating 124 to provide a non-slip ground contact surface. Attached to the front sides, and extending across the foot shell 128 is a toe retainer 116 preferably fabricated from a flexible polyethylene-type material with an upper Velcro® surface, or a forefoot retainer 136 with ladder strap and ratchet 114. Attached to rear sides of the skate shell 128 are a pair (left and right, medial and lateral) adjustable stirrups 118. Alternatively, as shown in the embodiments of FIGS. 10-16 a straight vertical bar 1182 which serves the same purpose. Extending upward therefrom are vertical extensions, uprights, or struts 120, 1202 each with an adjustable (rotatable) ankle hinge 1212 which, in use, is located external to, and adjacent to, the user's anatomical ankle joint (the rotatable connection between the lower ends of the tibia and fibula and the talus (i.e., the ankle joint)). An example of such a strut 120,1202 with hinge 1212 is commercially available from Becker® Orthopedic, Troy, MI 48083. These hinges can allow the clinician to control ankle range of motion into dorsi-flexion and plantar-flexion to meet patients' changing biomechanical needs. The hinges are adjustable using set screws with infinite positions thru their adjustment range which typically corresponds to normal ankle range of motion. Various inserts can be employed in the hinge chambers to allow, resist or block the user's ankle motion. These may be pins, springs or combinations thereof as determined by the clinician. Similar hinge designs are available from other manufacturers and could be incorporated instead of Becker hinges. Positioned between the toe retainer 116 or forefoot retainer 136 and the adjustable stirrups 118 or straight vertical bar 1182 and attached to the foot shell 128 is an adjustable ankle strap 114. A preferred embodiment of the adjustable ankle strap 114 is a strap used on a ski or snow board to retain a boot which incorporates a ladder strap, ratchet and locking buckle 115 with release mechanism. Connectors 126, such as rivets, screws, or nuts and bolts, etc.) are used to temporarily or permanently attach various components (the toe retainer 116, the stirrups 118, the bar 1182, the ankle strap 114, etc.) to the skate shell 128. Alternatively, various components may be integrated within the SKATE™ manufacturing process into the SKATE™ shell thru molding, slotting, or trimming to incorporate the specific design feature(s).

A rigid calf band 134 or pretibial band 102 with a padded liner 104 is positioned at the upper end of, and connecting, the right and left (medial and lateral) struts 1202, 120. The rigid calf band 134 and pretibial band 102 on the SKATE™ 100, 200 serve to maintain the medial and lateral (right and left) ankle hinge system in parallel alignment to each other and are individually contoured to match the user's anatomy. Attached to the calf band 134 and the pretibial band 102 is a closure such as a fabric backed Velcro® closure 106, with a stabilizing buckle 108. The combination of the foot shell 128, the struts 120,1202 with ankle hinges 1212, and the calf strap 134, Velcro® closure 106, stabilizing buckle 108 and exterior pretibial band 102 can have different configurations to allow for toe-first or heel-first placement as well as added varus or valgus control. Attached to one of the struts 1202 is ankle control strap 110 which includes a Velcro covered surface and a D-shaped ring or loop 111 (see FIG. 5) which can be grasped by the user to provide leverage in donning the SKATE™ assembly 100, 200. Placement of ankle control strap 110 on medial or lateral struts 1202 will be determined by the clinician for varus or valgus control configuration on either the SKATE™ 100 or 200.

FIGS. 10-16 show an anterior entry SKATE™ Support System 200. While the Skate foot shell 128 can be the same for posterior or anterior entry, a primary difference between the anterior entry and the posterior entry embodiments is that the anterior entry embodiments include a raised rear portion 140 of the foot shell 128 to prevent the shoe heel from sliding off the foot shell 128 and/or a heel retaining strap 138 attached to a rear portion of the foot shell 128 mounted to allow an increased grasp onto the user's shoe by tightening the clinician selected closure 114. Also, the toe retainer 116 can be replaced by a forefoot retainer 136. Mounted to the left (medial) strut 120 is an ankle strap 110 with a forward opening Velcro® hook and loop closure positioned to allow heel-first entry. The calf strap 102 likewise uses a Velcro® closure 106 configured to allow heel first placement (the openable portion faces forward). While Velcro® closures are fixed in place when closed, the ladder strap closures 114 provide the advantage of allowing incremental tightening and repositioning of the extremity during application. The purpose of this embodiment and construction is to provide stability to the injured foot following donning of the SKATE™ Support System by the user without aid of a second person.

FIGS. 1-16 provide different views and illustrate various embodiments of the SKATE™ Support System 100, 200 with different strap retaining structures added to the SKATE™ Support System 100, 200. More particularly, the different retaining structures are added to the foot shell 128, and/or the medial and lateral vertical struts 120, 1202 to accommodate toe or heel entry and vertical and horizontal alignments of the injured limb during the healing process.

Attached to each of the ankle hinges 1212 and extending upward therefrom, in various embodiments are the upright struts 120,1202 with an ankle control strap 110 attached to one of the upright struts 120,1202 and a calf strap 102, 134 attached to both upright struts 120, 1202 at their upper end. The SKATE™ Support System 100, 200 is designed to incorporate various custom molded pre-tibial shells or posterior calf shells to further improve ankle and knee stability and anterior swing bands to facilitate donning. A Patellar Tendon Bearing (PTB) or calf lacer design (not shown) may be incorporated to load the foot, ankle or tibia axially as may be medically indicated. A further embodiment (not shown) adds a proximal thigh extension incorporating various commercially available knee hinge designs.

FIG. 1 is a top view of a posterior entry embodiment for application of the SKATE™ Support System.

Figure 2:
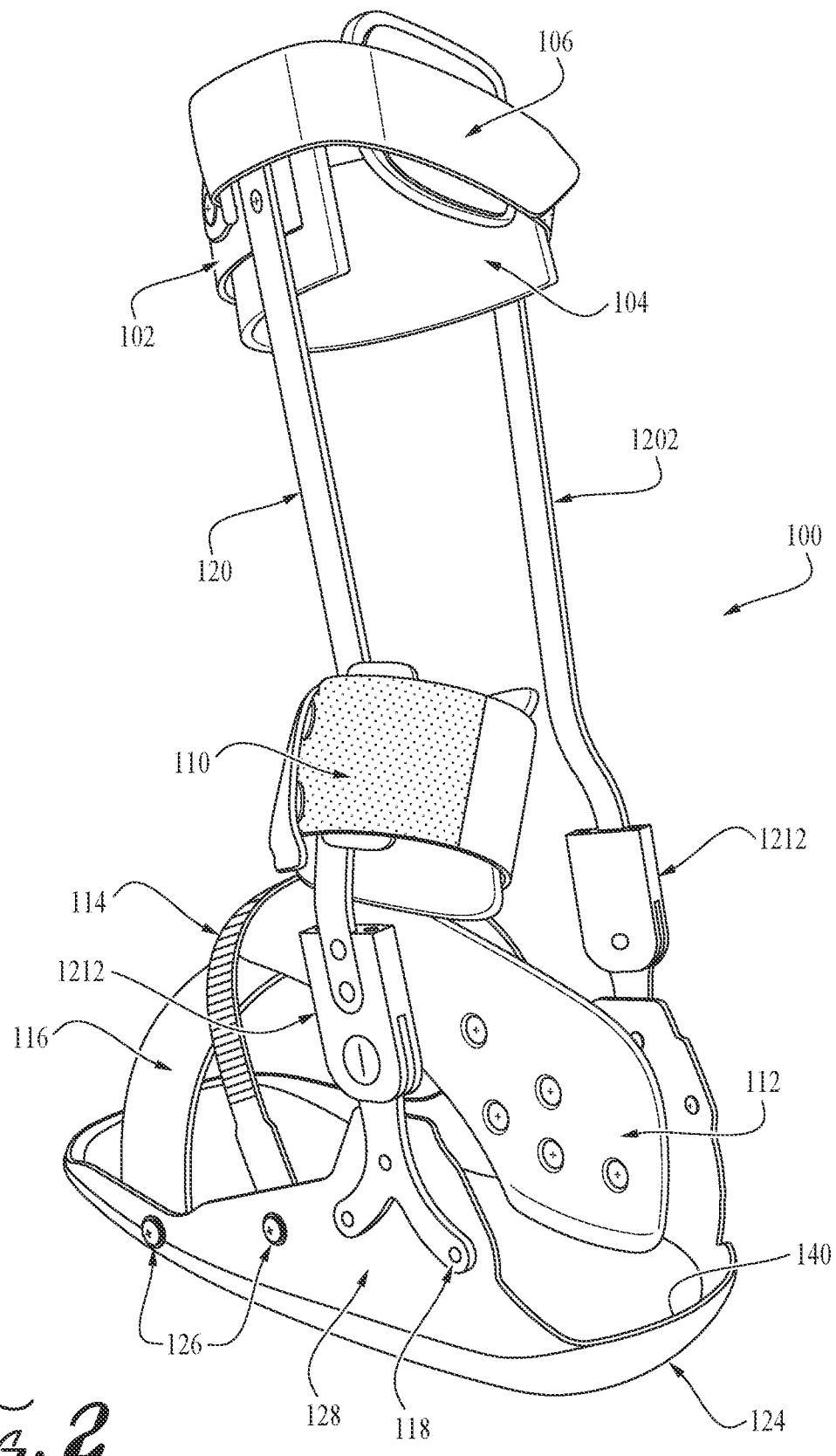

FIG. 2 is a right side medial perspective side view of the posterior entry SKATE™ Support System of FIG. 1.

Figure 3:
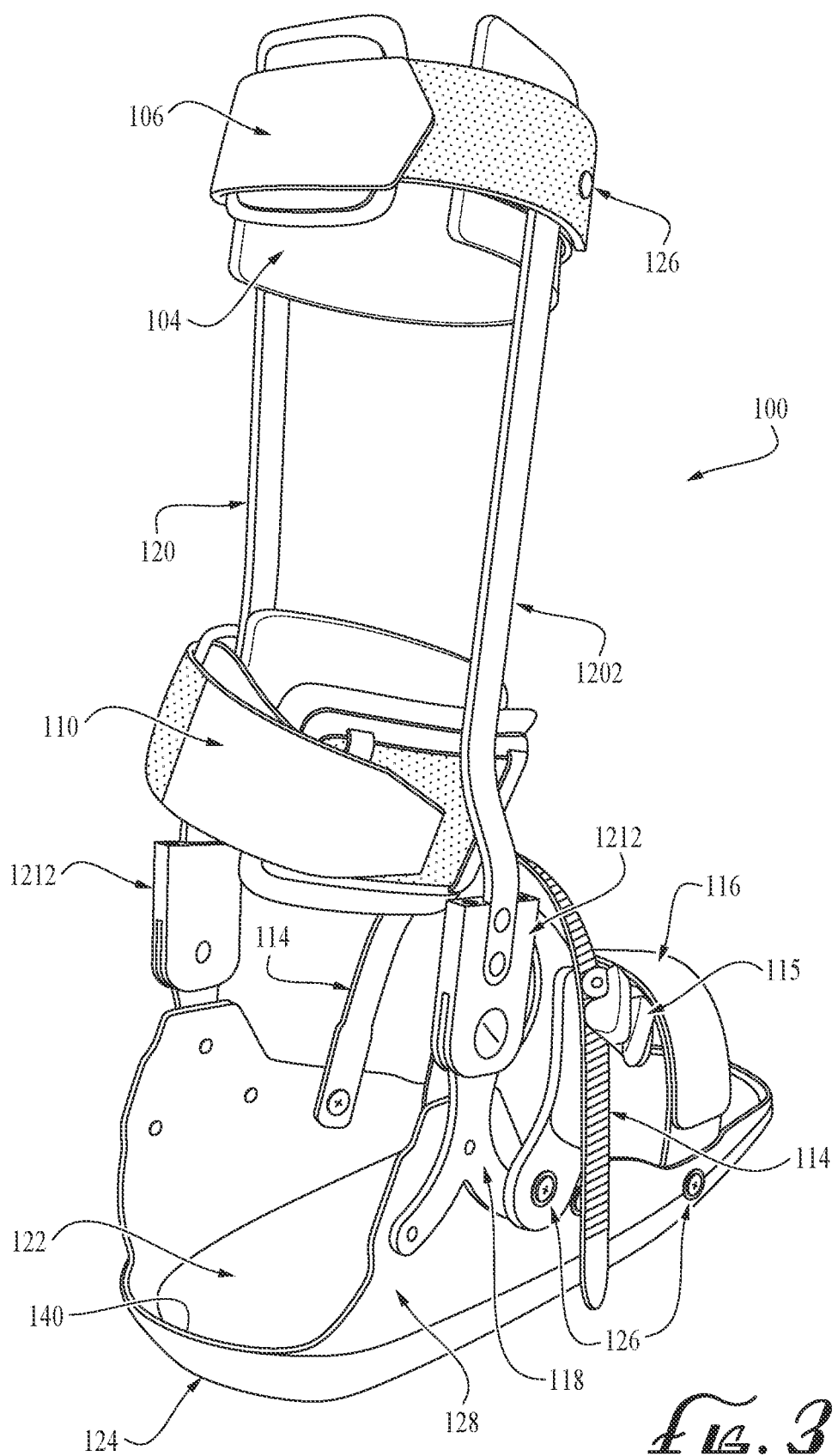

FIG. 3 is a right side lateral rear perspective view of the posterior entry SKATE™ Support System of FIG. 1.

Figure 4:
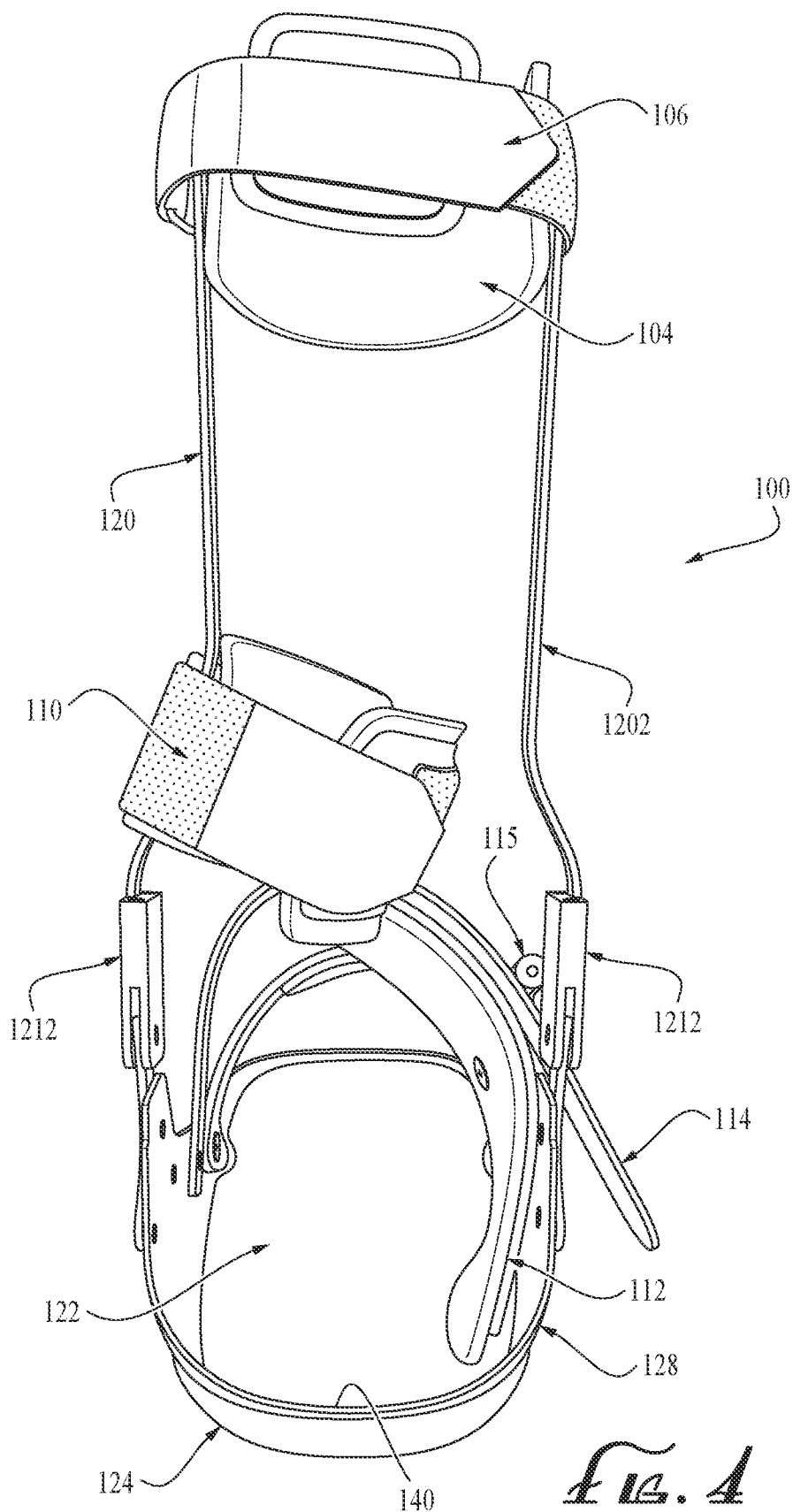

FIG. 4 is a rear view of the posterior entry SKATE™ Support System of FIG. 1.

Figure 5:
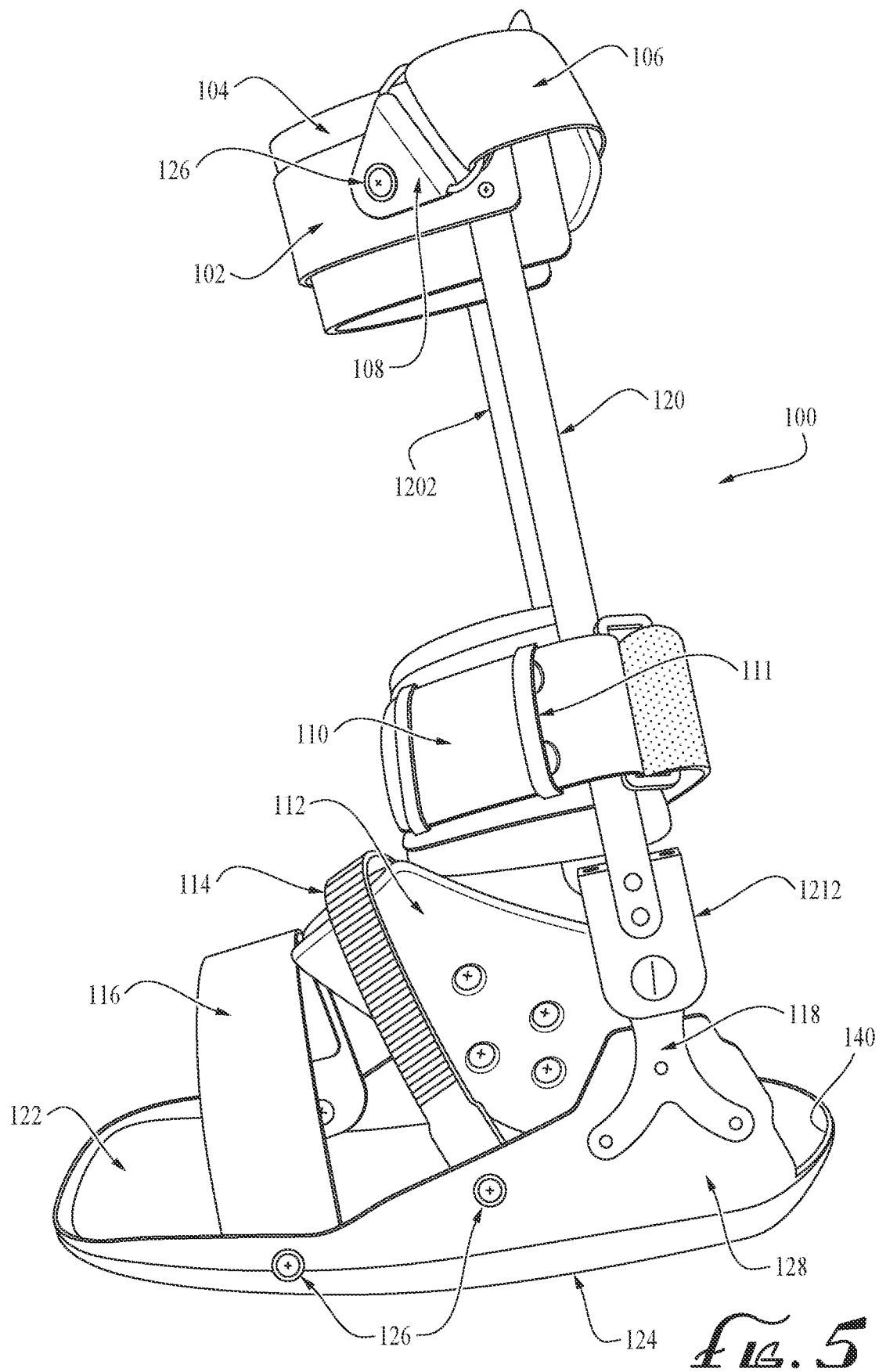

FIG. 5 is a right-side medial view of the posterior entry SKATE™ Support System of FIG. 1.

Figure 6:
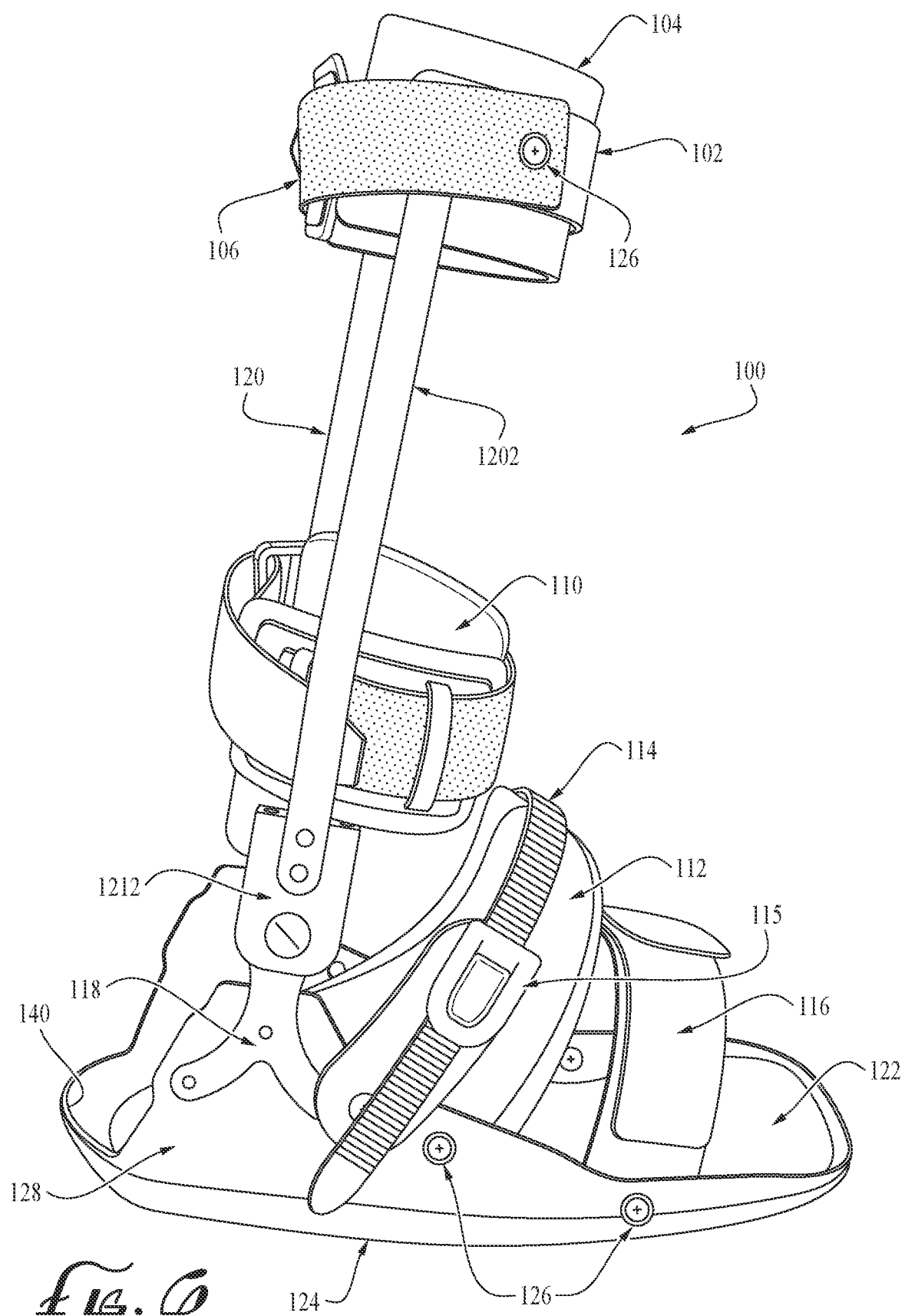

FIG. 6 is a right-side lateral view of the posterior entry SKATE™ Support System of FIG. 1.

Figure 7:
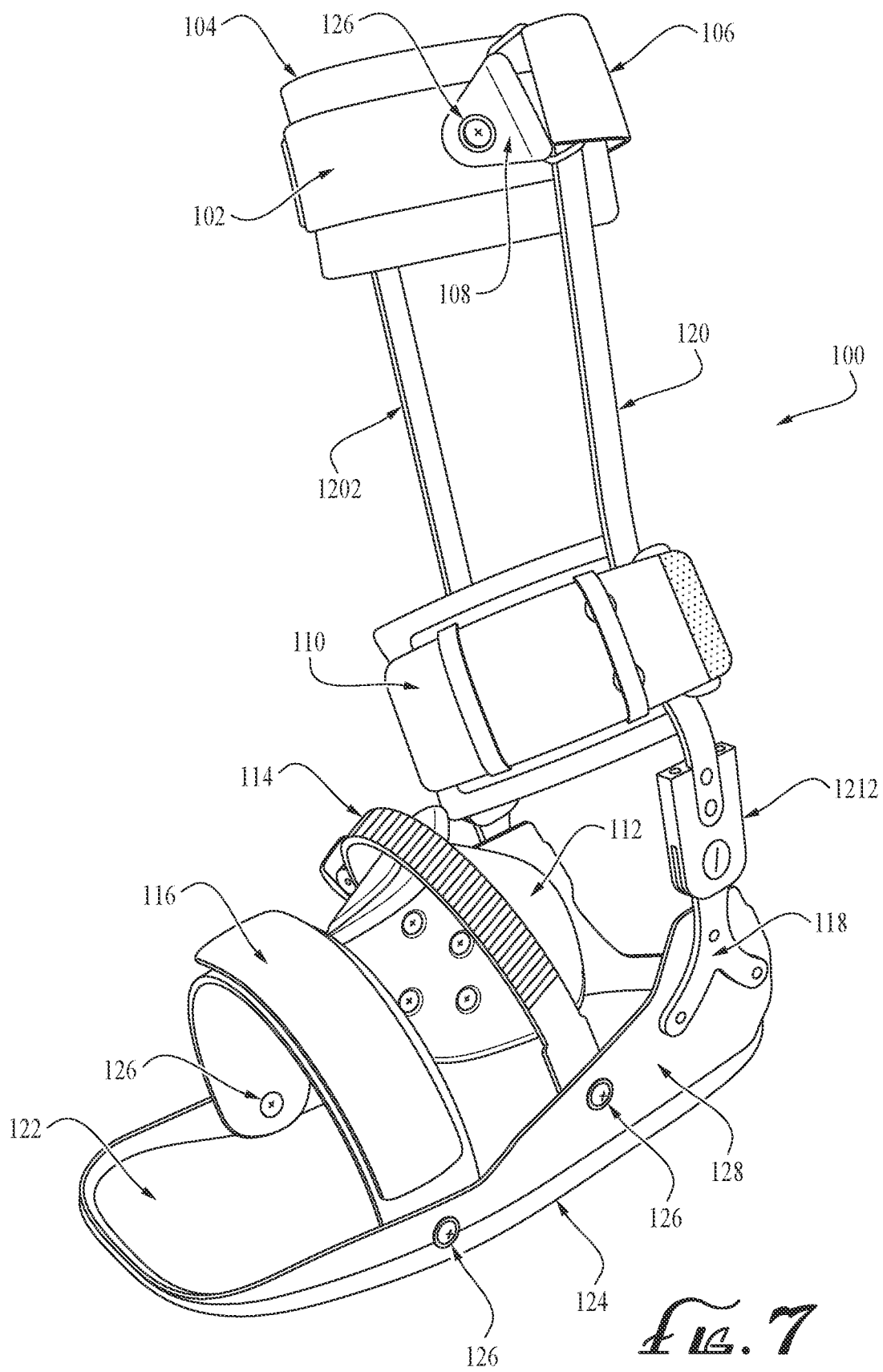

FIG. 7 is a right side medial anterior perspective view of the posterior entry SKATE™ Support System of FIG. 1.

Figure 8:
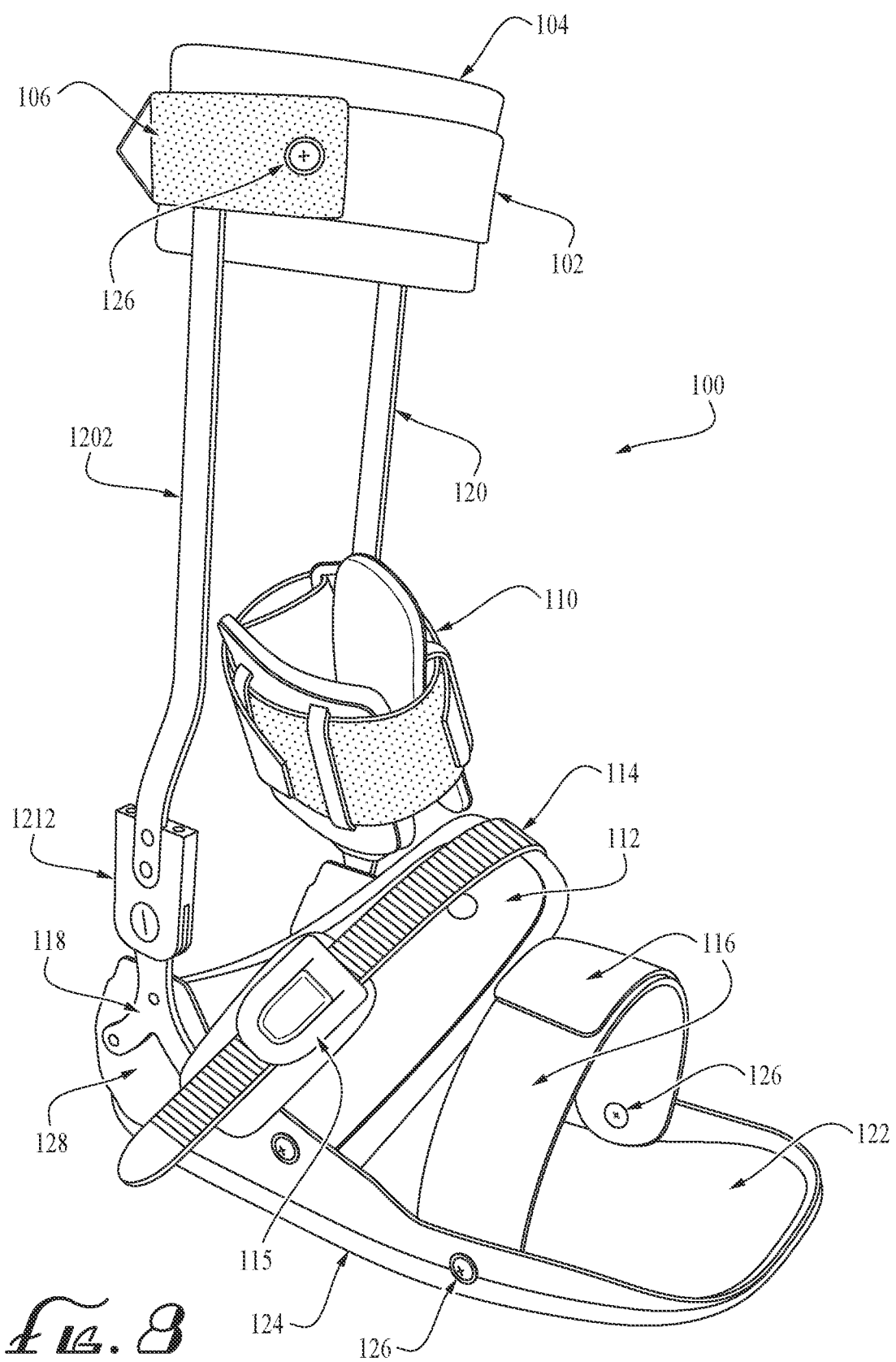

FIG. 8 is a right side lateral perspective view of the posterior entry SKATE™ Support System of FIG. 1.

Figure 9:
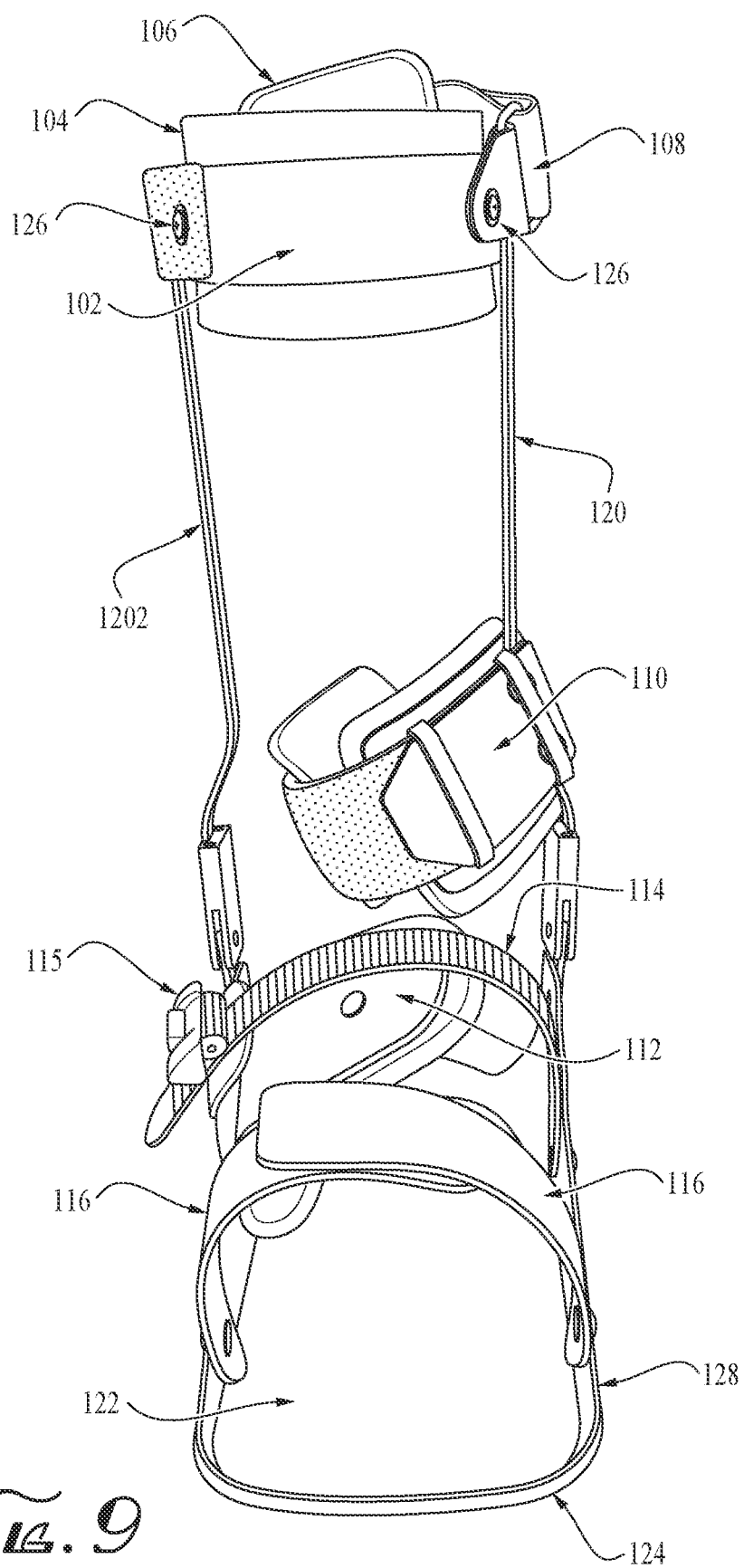

FIG. 9 is a front view of the posterior entry SKATE™ Support System of FIG. 1.

FIG. 10 is a top view of an anterior entry SKATE™ Support System.

Figure 11:
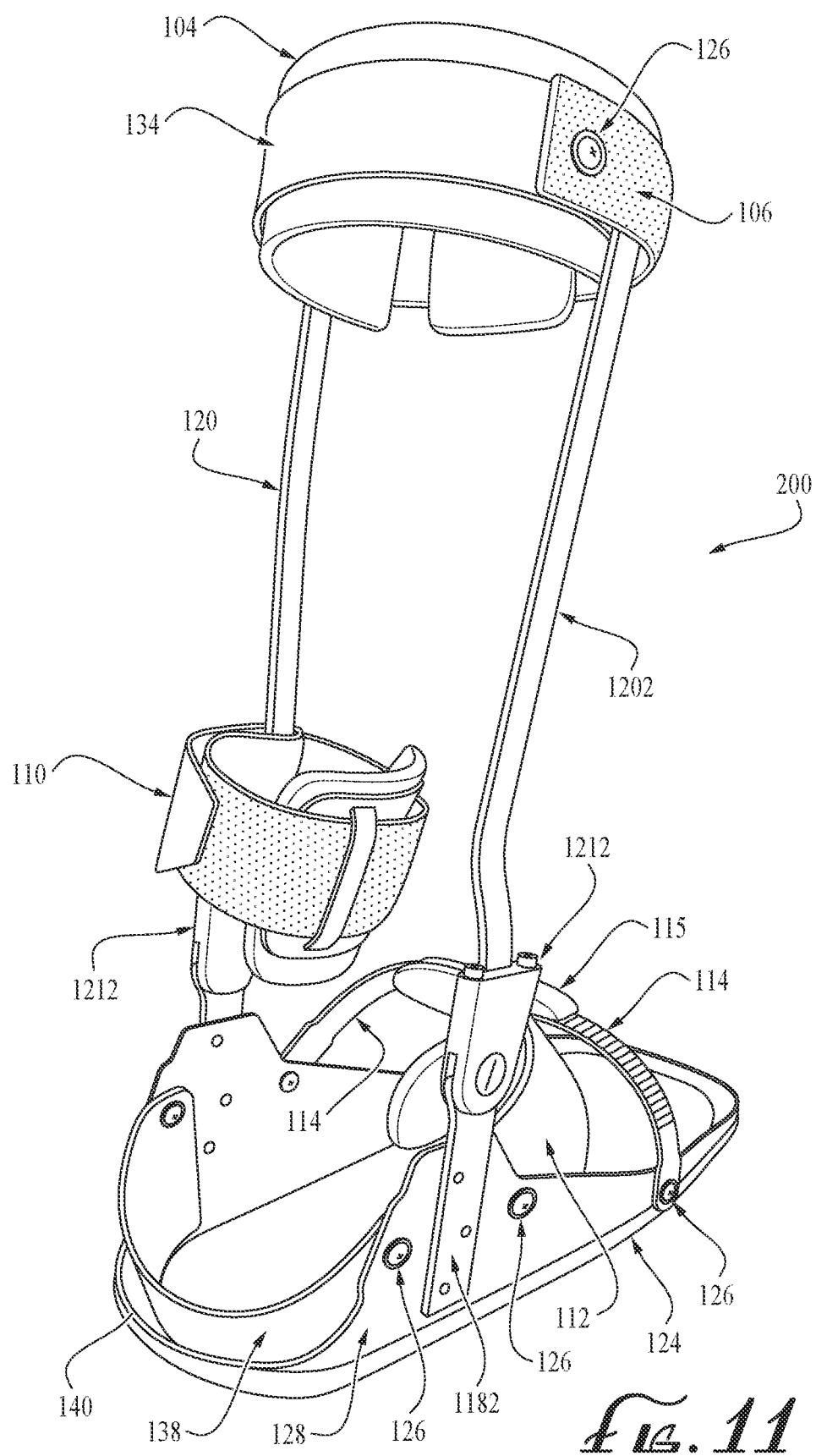

FIG. 11 is a right side lateral rear perspective view of an anterior entry SKATE™ Support System of FIG. 10.

Figure 12:
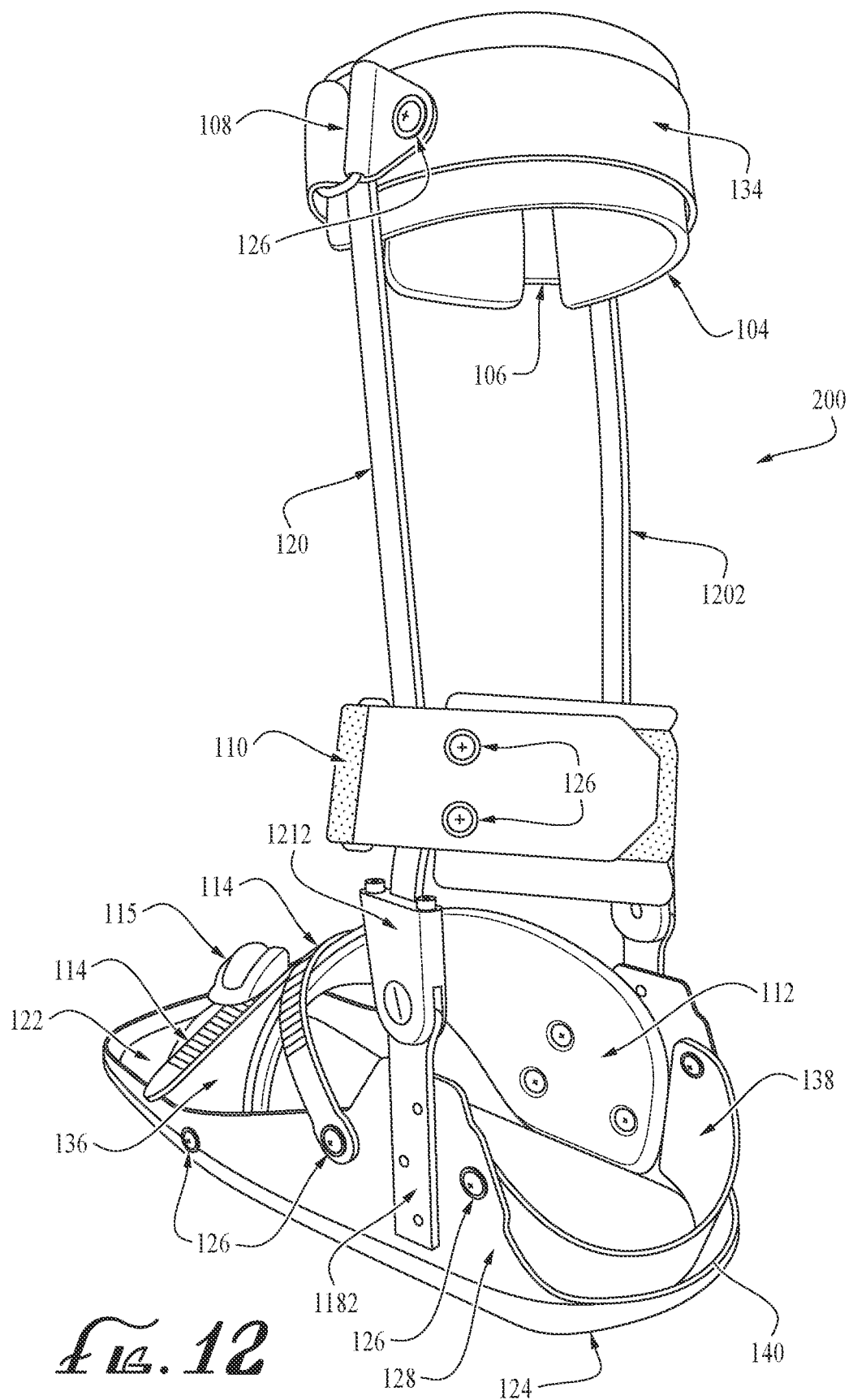

FIG. 12 is a right side medial rear perspective view an anterior entry SKATE™ Support System of FIG. 10.

Figure 13:
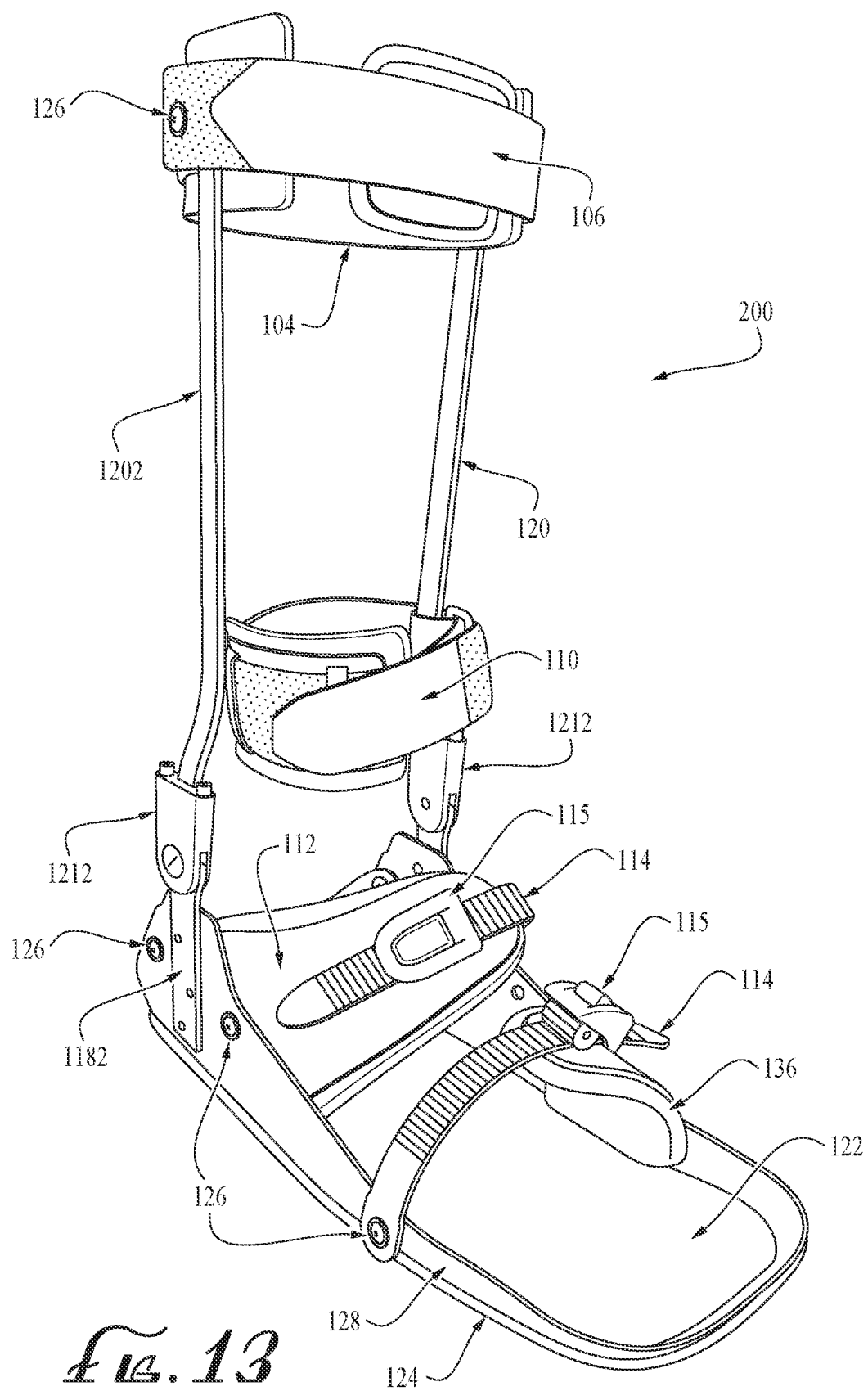

FIG. 13 is a right side front lateral perspective view of an anterior entry SKATE™ Support System of FIG. 10.

Figure 14:
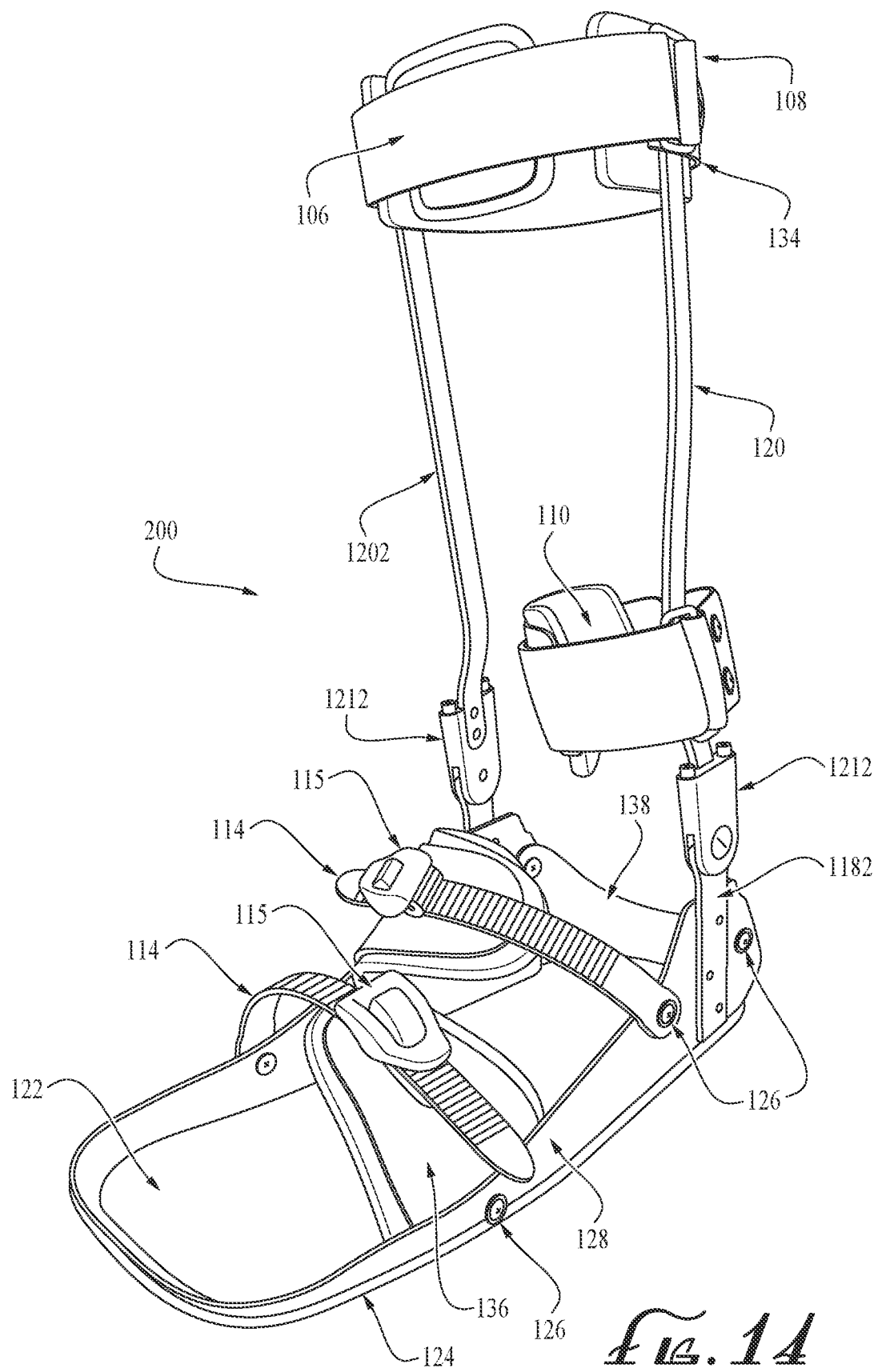

FIG. 14 is a right side front medial perspective view of an anterior entry SKATE™ Support System of FIG. 10.

Figure 15:
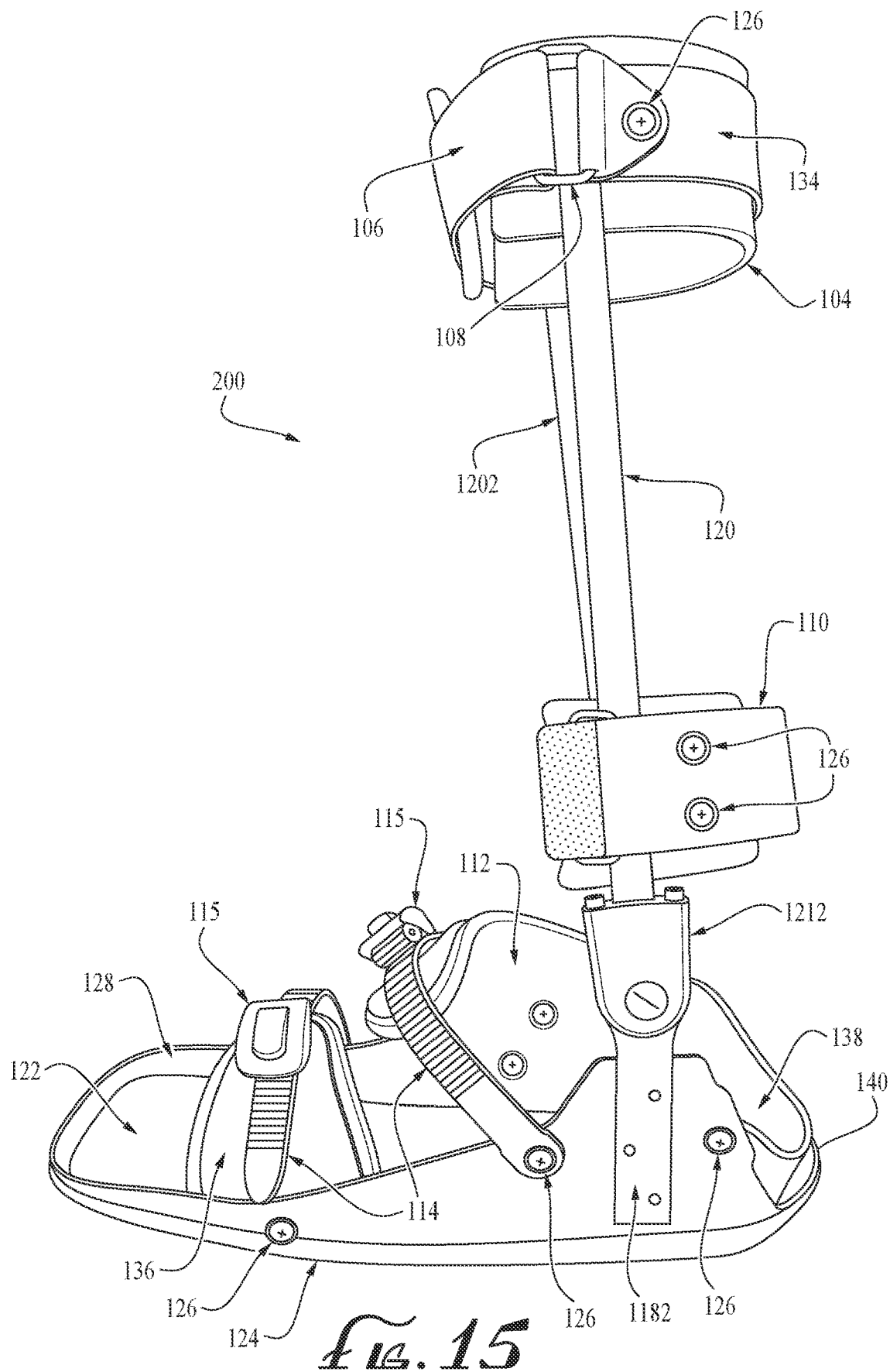

FIG. 15 is a right side medial view of an anterior entry SKATE™ Support System of FIG. 10.

FIG. 16 is a posterior view of a right side anterior entry SKATE™ Support System of FIG. 10.

The SKATE™ Support System 100, 200 described above and shown in the Figures can be configured and applied to either the right or left leg, for either varus or valgus pressure application, with either anterior or posterior entry for donning and biomechanical needs and the various closures can be configured for ease of the user to apply and tighten the straps using either the left or right hand. However, a preferred arrangement for right foot placement is to have the latching mechanism primarily accessible by the user's right hand; left foot placement preferably provides for left hand tightening of the straps. Closures may be intentionally reversed to allow sound side hand operation or improved visibility of closures by the patient and caregiver(s) as determined by the dispensing clinician or patient preference.

The pretibial band 102 or posterior portion of the calf strap 134 can be traditional metal, custom molded thermoplastics or composites based on the requirements of the patient's injury. The pretibial band can also be replaced with a Patellar Tendon Bearing (PTB) design to aid in axially offloading the ankle and/or foot regions, it can also be replaced with an anterior swing band to ease donning. The approach of applying an orthosis over the shoes most often will require use of a compensatory lift in the shoe on the uninjured limb of approximately 1 cm to compensate for the height of the foot shell 128.

Closures and straps are specifically designed and/or selected to allow ease of donning/doffing of the SKATE™ Support System 100, 200 by the user using a single hand and are oriented on the SKATE™ Support System 100, 200 to support against either a varus or valgus ankle displacement. Closure orientations and locations are customized and vary based upon pre-tibial or posterior or anterior designs. These closures can include: Velcro™ hook-loop straps, ratcheting dial (NoVel™ or BOA™ systems) or snow board type ladder straps 114 and buckles 115. Low friction pads and liners positioned in contact with the patient's limbs are designed to fit over the shoe gear. This allows the patient's shoe gear to act as a "padded liner" or "interface" for the patient's foot and leg.

The SKATE shell 128 preferably comprises a molded aluminum skate, or shell, which serves as the platform to receive the user's shoe and as a limb foundation to provide improved gait and/or stability. Alternate skate foot shell materials can include titanium, thermoplastics and composites or similar durable materials and can be incorporated thru additive manufacturing or established manufacturing techniques. The other components used in assembling the SKATE™ Support System 100, 200 including, but not limited to the struts, straps, closures and pads, are often commercially available devices used in sports equipment or other orthotic devices but are modified to meet the specific structural and support requirements to properly construct the SKATE™ Support System 100, 200 for the particular needs of each patient. In particular, unnecessary holes in commercially available components which can weaken the structure have been removed (filled in) or the parts have been reconstructed without the unnecessary openings. For example, Becker® double adjustable stirrups have been reconfigured to meet the requirements of the skate shell. A neoprene sole 124 or similar material is applied to the bottom of the Skate shell 128 to provide a suitable ground contacting surface; a customized rocker bottom with a midstance "flat spot" for increased stability is also formed in the neoprene sole. The neoprene sole may incorporate additional modifications such as wedges, sole offsets, elevations, and modified rocker profiles according to clinician specified requirements. This SKATE shell 128 is customized to the individual gait profile and need of the patient and is designed to provide for either toe entry or heel entry. While constructed as thin as possible, it may require approximately 1 cm elevation spacers in the sound side shoe. This has not been a problem for any of the test subjects. However, all test subjects have felt that it was easier to add a spacer than oversizing the shoes on the non-booted foot and could be easily accommodated into their existing shoe gear.

While the number of different size SKATE shells 128 is not limited it has been generally found that four different sized metal SKATE shells 128 were adequate to meet most adult customer needs and are neutral (fit right or left legs); alignment, size and design variations are accommodated in the custom fabrication of the SKATE™ Support System 100, 200 upper portion by the pretibial or posterior calf designs along with custom modifications to the SKATE shell 128. Pediatric appropriate sizing, colors, and aesthetic options of SKATE™ Support Systems 100, 200 will follow the same biomechanical, clinical design and application rationale. The SKATE™ Support System 100, 200 calf/leg portion is custom fabricated using a profile tracing, cast mold, or digital scan/image and measurements to optimize alignment in all planes. In the various embodiments of the SKATE™ Support Systems 100, 200 the entire calf portion can also be replaced with a Patellar Tendon Bearing (PTB) design to aid in axial offloading of the ankle, and/or foot regions. The Patellar Tendon Bearing (PTB) design can be incorporated to either anterior or posterior entry design. An additional embodiment of the SKATE™ Support System 100, 200 incorporates a calf lacer design to stabilize volume and soft tissues and further distribute pressures. All calf portion designs contain a rigid member interconnecting the medial and lateral uprights or struts to maintain the hinges in congruent, parallel alignment.

The stirrups 118 or straight mount bars 1182 attached to the SKATE shell 128 are typically stainless steel. The hinges 1212 are specified by the clinician, and may be aluminum, stainless, titanium or similar durable material. The upright struts 120, 1202 can be aluminum, stainless steel, or composite materials depending on the clinician's requirements and patient needs.

Closure selections are customized for each individual application and are determined by the clinician based on patient bio-mechanical need for either pre-tibial or posterior shells/cuffs, alignment control for varus/valgus, manual dexterity, contrast for visual acuity, degree of gait stability required and unit cost. Velcro™ attachments are often used because they are often the least costly. While NoVel™ closures, BOA reel or dial closures, and ladder straps are more costly, they are also suitable because they each have unique advantages. In particular, these closure designs have the advantage of providing incremental tightening during donning, allowing tightening, re-positioning, additional tightening, and additional repositioning for optimal alignment in greater requirement patients.

There are several populations that are not served well with current orthosis designs; these are better served by the SKATE™ Support System 100, 200. The first is the very low level, standing pivot transfer-limited household ambulator type patient. They will benefit from a device that improves ankle stability and standing balance and provides greater therapeutic or household ambulation. The patient will also benefit from the device during transport to medical visits, family, and community visits to reduce fall risks and caregiver risk. However, these patients are often not prescribed a device due to low anticipated usage/compliance, level of dependence requiring caregiver assistance, potential pressure risks, complexity with shoe gear issues etc. Frequently, current art remains unused due to challenges associated with potential pressure areas, donning difficulty, follow-up and adjustment difficulty, caregiver, and patient compliance.

A further alternative use is for the early post-acute rehab patient. Because such a device is not completely disruptive to their dressing and clothing routine, and can employ existing shoe gear, it can be prescribed and dispensed in a timely manner with minimal follow-up required and reduced risk of complications post discharge allowing timely discharge from a treatment facility. The SKATE™ Support System 100, 200 can be worn over existing shoegear and clothing thus easing donning and doffing requirements. The SKATE™ Support System 100, 200 merely requires a tracing or limb scan which can be transmitted with specific measurements for rapid fabrication. This custom device can be fabricated in ideal circumstances, for next day availability, but a three-day turnaround is more likely to address the reduced acute Rehab and therapy stays. The SKATE™ has served as a training/interim orthosis pending definitive design, fabrication and prescription of a custom internal AFO or external shoe AFO during rehabilitation.

A more recent potential application is as a base for high elevation leg length discrepancies such as in arthrogryposis and other focal hemimelias. Using a modified SKATE™ Support System 100, 200 a support with as much as a six inches added elevation can be provided for a very active user with the SKATE™ Support System 100, 200 fitted to accommodate a steel-toed work boot, eliminated the need to add an elevation to each pair of work boots while improving ankle stability.

For the extremely high functioning traumatic brain injury (TBI) or stroke (CVA) patient that can don/doff a device independently, the SKATE™ Support System 100, 200 provides an especially useful option enhancing patient lifestyles. Many of these patients wear an orthosis substantially full-time, and while they may in fact be capable of ambulating short distances without an orthosis, such movement is very slow and can have a considerable fall risk. Those patients frequently "just need a break" away from the constant, full time pressures, and may use the SKATE™ as an alternative if a pressure or sore area develops following extended use of a custom device. These patients may elect to wear the SKATE™ Support System 100, 200 in or around their home with their own lightweight sneakers/tennis and remove the SKATE™ Support System 100, 200 and relax on the couch, watch TV, etc. and then put on the System to answer the door, get something in kitchen and then remove it again to watch the game on TV. These individuals may not be functionally able to wear a slipper or house shoe safely for ambulation. Patients testing the SKATE™ Support System 100, 200 have stated they prefer the System 100, 200 for generalized home use but may use their custom device out in the community due to the greater gait efficiency generally provided by their custom orthoses. As long-term, often permanent, orthotic users, they also state they have worn the SKATE Support System while their own custom orthosis may be unavailable due to required repairs or during extensive adjustments and alterations, and during periods of healing following extended use of other devices which may have caused sensitive pressure points.

As a further alternative, the SKATE™ Support System 100, 200 can provide an additional treatment option in foot/ankle degenerative Arthritis and wound care environments for patients that also require an AFO. The SKATE™ Support System 100, 200 allows existing, costly, diabetic wound care footwear to be employed within the AFO, allows the AFO to be donned easily at minimal risk of additional pressure areas and provide accommodation for swelling volume fluctuation in addition to accommodating bulkier dressings around the lower leg. Many wound care patients can have a concurrent or contributory, functional lower limb weakness frequently caused by stroke, traumatic brain injury, neurological or orthopedic impairment and are not prescribed an AFO due to concerns about potential pressure areas, limited access to clinical care and follow-up and fitting needs. The SKATE support system can serve as alternative orthotic device to provide much needed stability during their extended wound care. Arthritic patients may use the device to reduce motion that exacerbates pain during routine ambulation and activities of daily living. They may use the SKATE™ system in a home, work or other environment as needed and easily remove when not required.

Other potential applications/modifications include use of custom thermoplastic pre-tibial and posterior calf shells, or full Patella tendon bearing (PTB) designs and/or full calf lacers for pressure distribution, axial ankle off-loading/trauma or to improve soft tissue stability. Another alternative is to use the SKATE™ Support System 100, 200 for ambulatory patients that may wish to remove their device quickly once they arrive at work, etc. while continuing with their work/dress shoe gear for lighter duty ambulatory activities.

A further alternative embodiment is the incorporation of the SKATE Support System 100/200 into a Knee Ankle Foot Orthosis (KAFO). This modification allows additional leverage and various knee hinge designs to be incorporated for additional knee stability. This modification could be employed for various diagnoses and biomechanical needs as determined by their clinician.

The SKATE™ Support System 100, 200 provides a unique a new product alternative that addresses an unmet need as well as being compatible with established manufacturing and distribution settings including orthotic facilities with metal fabrication, thermoplastic and composites fabrication capability. Existing clinical staff can assist with device design selection for customers following device prescription from a licensed physician. Customization by the dispensing clinician (most commonly an Orthotist/Prosthetist, Doctor of Podiatry, Medical Doctor or Doctor of Osteopathy) is required to determine the type of design, i.e., pre-tibial vs posterior shell, metal vs molded plastic, closure orientation for varus or valgus control and closure type, for example Velcro™, NoVel™, BOA™ reel or dial closures, or Ladder straps, to be coupled with custom SKATE™ shell 128 designs.

Further, the SKATE™ Support System 100, 200 fits into currently available coding schema and will be reimbursable under current Government payment criteria to the dispensing clinical provider, immediately benefitting patients, families, and caregivers. Stylistic options, such as closure and pad colors, bar and structure colors/coatings can be incorporated for aesthetic purposes. The SKATE™ Support System 100, 200 may also more easily accommodate patient weight changes (gain or loss) due to the more open, less restrictive design as well as functional gait and support changes during healing and recovery.

Other embodiments include pediatrically sized and aesthetically styled versions which incorporate identical or similar design features and functions. These meet the same clinical functional criteria and offer this population similar biomechanical benefits. The only change required is the SKATE™ foot shell sizing, hinge and stirrup and closure component sizing. Pediatric ankle hinge systems and ratchet type closure systems are currently commercially available which replicate adult function. These, as well as other modifications described herein, can be easily incorporated.

I claim:

1. An ankle foot orthosis (AFO) configured to receive a user's lower extremity having existing shoe gear thereon for varus control of an ankle, said AFO comprising:
    a foot shell having a first lateral surface, a second lateral surface, and an interior upper surface, the interior upper surface configured to be in contact with a lower surface of the existing shoe gear;
    a toe panel internally attached to the first lateral surface configured to be in medial contact with an upper exterior surface of the existing shoe gear;
    a toe strap externally attached to the second lateral surface;
    a varus control panel internally attached to the second lateral surface configured to be in lateral contact with the upper exterior surface of the existing shoe gear;
    a varus control strap externally attached to the first lateral surface;
    a medial elongated strut and a lateral elongated strut extending upwardly from the foot shell, said medial elongated strut being connected, at a lower portion thereof, to an external face of the first lateral surface of the foot shell by a first adjustable extension and a first adjustable hinge, said lateral elongated strut being connected, at a lower portion thereof, to an external face of the second lateral surface of the foot shell by a second adjustable extension and a second adjustable hinge, said first adjustable hinge and said second adjustable hinge both allowing for control of an ankle range of motion when in use;
    an ankle control strap connected to the medial elongated strut, encircling the medial elongated strut and not encircling the lateral elongated strut; and
    a calf band or a pretibial band attached to an upper portion of the medial elongated strut and the lateral elongated strut, the calf band or pretibial band being rigid and interconnecting the medial elongated strut and the lateral elongated strut to maintain the medial elongated strut and the lateral elongated strut in a congruent and parallel alignment,
    wherein the toe panel, the varus control panel, and the ankle control strap form a three point varus control pressure system.

2. The AFO of claim 1, wherein the first elongated strut, the second elongated strut, and the calf band or pretibial band are each custom contoured to match a user's anatomy.

3. The AFO of claim 1, wherein said first adjustable extension and said second adjustable extension are adjustable "Y" stirrups.

4. The AFO of claim 1, wherein said first adjustable extension and said second adjustable extension are straight bars.

5. The AFO of claim 1, wherein said first adjustable hinge and said second adjustable hinge are configured to be adjacent to a user's anatomical ankle joint during use.

6. The AFO of claim 1, wherein the varus control strap and the toe strap each comprise a ladder strap and a ratchet and are configured to be operated with one hand.

7. The AFO of claim 1, further comprising a non-slip coating on the bottom surface of the foot shell.

8. The AFO of claim 1, further comprising a heel retaining strap attached to the foot shell configured to contact the heel of the existing shoe gear.

9. The AFO of claim 1, wherein an interior face of the first lateral surface and an interior face of the second lateral surface of the foot shell are smooth, such that the existing shoe gear can slide into the foot shell.

10. The AFO of claim 1, wherein the AFO is configured for a heel-first anterior entry, wherein the calf band interconnects the first elongated strut and the second elongated strut, and a rear portion of the foot shell is raised.

11. The AFO of claim 1, wherein a length of the foot shell is greater than a length of the existing shoe gear.

12. A method of installing an ankle foot orthosis (AFO) on a user's lower extremity having an existing shoe gear thereon for varus control of an ankle, said method comprising:
    receiving a user's foot encased in the existing shoe gear;
    inserting the existing shoe gear into a foot shell, said foot shell having a first lateral surface, a second lateral surface, and an interior upper surface, the interior upper surface configured to be in contact with a lower surface of the existing shoe gear;
    anchoring a toe panel and toe strap, the toe panel internally attached to the first lateral surface configured to be in medial contact with an upper exterior surface of the existing shoe gear and the toe strap externally attached to the second lateral surface;
    anchoring a varus control panel and varus control strap, the varus control panel internally attached to the second lateral surface configured to be in lateral contact with the upper exterior surface of the existing shoe gear and the varus control strap externally attached to the first lateral surface; and
    anchoring an ankle control strap, the ankle control strap connected to a medial elongated strut, encircling the medial elongated strut and not encircling a lateral elongated strut;
    said AFO comprising the medial elongated strut and the lateral elongated strut extending upwardly from the foot shell and a calf band or pretibial band attached to an upper portion of the medial elongated strut and the lateral elongated strut, the calf band or pretibial band being rigid and interconnecting the medial elongated strut and the lateral elongated strut to maintain the medial elongated strut and the lateral elongated strut in a congruent and parallel alignment, said medial elongated strut being connected, at a lower portion thereof, to an external face of a first lateral surface of the foot shell by a first adjustable stirrup and a first adjustable hinge, said lateral elongated strut being connected, at a lower portion thereof, to an external face of a second lateral surface of the foot shell by a second adjustable stirrup and a second adjustable hinge, said first adjustable hinge and said second adjustable hinge both allowing for control of an ankle range of motion when in use, wherein the toe panel, the varus control panel, and the ankle control strap form a three point varus control pressure system.

13. The method of claim 12, wherein, when the pretibial band is attached to the upper portion of the medial elongated strut and the lateral elongated strut, the user's foot encased in the existing shoe gear is received in the AFO by a posterior entry.

14. The method of claim 12, wherein, when the calf band is attached to the upper portion of the medial elongated strut and the lateral elongated strut, the user's foot encased in the existing shoe gear is received in the AFO by an anterior entry.

15. An ankle foot orthosis (AFO) configured to receive a user's lower extremity having existing shoe gear thereon for valgus control of an ankle, said AFO comprising:
  a foot shell having a first lateral surface, a second lateral surface, and an interior upper surface, the interior upper surface configured to be in contact with a lower surface of the existing shoe gear;
  a toe panel internally attached to the second lateral surface configured to be in lateral contact with an upper exterior surface of the existing shoe gear;
  a toe strap externally attached to the first lateral surface;
  a valgus control panel internally attached to the first lateral surface configured to be in medial contact with the upper exterior surface of the existing shoe gear;
  a valgus control strap externally attached to the second lateral surface;
  a medial elongated strut and a lateral elongated strut extending upwardly from the foot shell, said medial elongated strut being connected, at a lower portion thereof, to an external face of the first lateral surface of the foot shell by a first adjustable extension and a first adjustable hinge, said lateral elongated strut being connected, at a lower portion thereof, to an external face of the second lateral surface of the foot shell by a second adjustable extension and a second adjustable hinge, said first adjustable hinge and said second adjustable hinge both allowing for control of an ankle range of motion when in use;
  an ankle control strap connected to the lateral elongated strut, encircling the lateral elongated strut and not encircling the medial elongated strut; and
  a calf band or a pretibial band attached to an upper portion of the medial elongated strut and the lateral elongated strut, the calf band or pretibial band being rigid and interconnecting the medial elongated strut and the lateral elongated strut to maintain the medial elongated strut and the lateral elongated strut in a congruent and parallel alignment,
  wherein the toe panel, the valgus control panel, and the ankle control strap form a three point valgus control pressure system.

16. The AFO of claim 15, wherein the first elongated strut, the second elongated strut, and the calf band or pretibial band are each custom contoured to match a user's anatomy.

17. The AFO of claim 15, wherein said first adjustable extension and said second adjustable extension are adjustable "Y" stirrups.

18. The AFO of claim 15, wherein said first adjustable extension and said second adjustable extension are straight bars.

19. The AFO of claim 15, wherein said first adjustable hinge and said second adjustable hinge are configured to be adjacent to a user's anatomical ankle joint during use.

20. The AFO of claim 15, wherein the valgus control strap and the toe strap each comprise a ladder strap and a ratchet and are configured to be operated with one hand.

21. The AFO of claim 15, further comprising a non-slip coating on the bottom surface of the foot shell.

22. The AFO of claim 15, further comprising a heel retaining strap attached to the foot shell configured to contact the heel of the existing shoe gear.

23. The AFO of claim 15, wherein an interior face of the first lateral surface and an interior face of the second lateral surface of the foot shell are smooth, such that the existing shoe gear can slide into the foot shell.

24. The AFO of claim 15, wherein the AFO is configured for a heel-first anterior entry, wherein the calf band interconnects the first elongated strut and the second elongated strut, and a rear portion of the foot shell is raised.

25. The AFO of claim 15, wherein a length of the foot shell is greater than a length of the existing shoe gear.

26. A method of installing an ankle foot orthosis (AFO) on a user's lower extremity having an existing shoe gear thereon for valgus control of an ankle, said method comprising:
  receiving a user's foot encased in the existing shoe gear;
  inserting the existing shoe gear into a foot shell, said foot shell having a first lateral surface, a second lateral surface, and an interior upper surface, the interior upper surface configured to be in contact with a lower surface of the existing shoe gear;
  anchoring a toe panel and toe strap, the toe panel internally attached to the second lateral surface configured to be in lateral contact with an upper exterior surface of the existing shoe gear and the toe strap externally attached to the first lateral surface;
  anchoring a valgus control panel and valgus control strap, the valgus control panel internally attached to the first lateral surface configured to be in medial contact with the upper exterior surface of the existing shoe gear and the valgus control strap externally attached to the second lateral surface; and
  anchoring an ankle control strap, the ankle control strap connected to a lateral elongated strut, encircling the lateral elongated strut and not encircling a medial elongated strut;
  said AFO comprising the medial elongated strut and the lateral elongated strut extending upwardly from the foot shell and a calf band or pretibial band attached to an upper portion of the medial elongated strut and the lateral elongated strut, the calf band or pretibial band being rigid and interconnecting the medial elongated strut and the lateral elongated strut to maintain the medial elongated strut and the lateral elongated strut in a congruent and parallel alignment,
  said medial elongated strut being connected, at a lower portion thereof, to an external face of a first lateral surface of the foot shell by a first adjustable stirrup and a first adjustable hinge, said lateral elongated strut being connected, at a lower portion thereof, to an external face of a second lateral surface of the foot shell by a second adjustable stirrup and a second adjustable hinge, said first adjustable hinge and said second adjustable hinge both allowing for control of an ankle range of motion when in use, wherein the toe panel, the valgus control panel, and the ankle control strap form a three point valgus control pressure system.

27. The method of claim 26, wherein, when the pretibial band is attached to the upper portion of the medial elongated strut and the lateral elongated strut, the user's foot encased in the existing shoe gear is received in the AFO by a posterior entry.

28. The method of claim 26, wherein, when the calf band is attached to the upper portion of the medial elongated strut and the lateral elongated strut, the user's foot encased in the existing shoe gear is received in the AFO by an anterior entry.

* * * * *